US011340236B2

(12) United States Patent
Snider et al.

(10) Patent No.: US 11,340,236 B2
(45) Date of Patent: *May 24, 2022

(54) METHODS FOR TREATING OR PREDICTING RISK OF A VENTRICULAR TACHYARRHYTHMIA EVENT

(71) Applicants: Critical Care Diagnostics, Inc., San Diego, CA (US); Cardiac Pacemakers, Inc., Saint Paul, MN (US)

(72) Inventors: James V. Snider, San Diego, CA (US); Timothy Edward Meyer, North Oaks, MN (US); Craig Michael Stolen, New Brighton, MN (US); Robert W. Gerwien, Newington, CT (US)

(73) Assignees: Critical Care Diagnostics, Inc., San Diego, CA (US); Cardiac Pacemakers, Inc., St. Paul, MN (US)

( * ) Notice: Subject to any disclaimer, the term of this patent is extended or adjusted under 35 U.S.C. 154(b) by 314 days.

This patent is subject to a terminal disclaimer.

(21) Appl. No.: 16/563,510

(22) Filed: Sep. 6, 2019

(65) Prior Publication Data
US 2019/0391162 A1  Dec. 26, 2019

Related U.S. Application Data

(63) Continuation of application No. 15/370,049, filed on Dec. 6, 2016, now Pat. No. 10,408,845, which is a
(Continued)

(51) Int. Cl.
*G01N 33/68* (2006.01)
*A61B 5/00* (2006.01)
(Continued)

(52) U.S. Cl.
CPC ....... *G01N 33/6887* (2013.01); *A61B 5/7275* (2013.01); *A61N 1/3627* (2013.01);
(Continued)

(58) Field of Classification Search
CPC ......... G01N 33/6887; G01N 2800/326; G01N 2800/50; A61N 1/362; A61B 5/7275
See application file for complete search history.

(56) References Cited

U.S. PATENT DOCUMENTS 7,432,060 B2   10/2008   Lee
7,655,415 B2   2/2010    Lee
(Continued)

FOREIGN PATENT DOCUMENTS

CN   101517415   8/2009
CN   101790687   7/2010
(Continued)

OTHER PUBLICATIONS

MX Office Action in Mexican Appln. No. MX/a/2018/009019, dated Sep. 8, 2020, 8 pages (with English translation).
(Continued)

*Primary Examiner* — William H Matthews
(74) *Attorney, Agent, or Firm* — Fish & Richardson P.C.

(57) ABSTRACT

Provided herein are methods that include (i) determining a level of soluble ST2 in a biological sample from a subject, (i) comparing the level of soluble ST2 in the biological sample to a reference level of soluble ST2 (e.g., a level of soluble ST2 in the subject at an earlier time point), and (iii) selecting, implanting, replacing, or reprogramming an implanted cardiac device, e.g., an ICD, CRT, or CRT-D device, for a subject having an elevated level of soluble ST2 in the biological sample compared to the reference level of soluble ST2, or selecting a subject for participation in, or stratifying a subject participating in, a clinical study of a treatment for reducing the risk of a ventricular tachyarrhythmia (VTA) event. Also provided are methods for evaluating
(Continued)

the risk of a VTA event in a subject. Also provided are kits for performing any of these methods.

16 Claims, 5 Drawing Sheets

Specification includes a Sequence Listing.

Related U.S. Application Data continuation of application No. 13/897,249, filed on May 17, 2013, now abandoned.

(60) Provisional application No. 61/649,202, filed on May 18, 2012.

(51) Int. Cl.
*A61N 1/362* (2006.01)
*A61N 1/39* (2006.01)

(52) U.S. Cl.
CPC ........ *G01N 33/6893* (2013.01); *A61N 1/3956* (2013.01); *G01N 2333/7155* (2013.01); *G01N 2800/325* (2013.01); *G01N 2800/326* (2013.01); *G01N 2800/50* (2013.01)

(56) References Cited

U.S. PATENT DOCUMENTS

| | | | |
|---|---|---|---|
| 7,670,769 | B2 | 3/2010 | Lee |
| 7,985,558 | B2 | 7/2011 | Lee |
| 7,989,210 | B2 | 8/2011 | Lee |
| 7,998,683 | B2 | 8/2011 | Snider et al. |
| 8,090,562 | B2 | 1/2012 | Snider et al. |
| 8,420,785 | B2 | 4/2013 | Snider et al. |
| 8,530,173 | B2 | 9/2013 | Lee |
| 8,597,958 | B2 | 12/2013 | Lee |
| 8,617,825 | B2 | 12/2013 | Snider et al. |
| 8,728,742 | B2 | 5/2014 | Snider |
| 8,734,769 | B2 | 5/2014 | Lee |
| 8,748,110 | B2 | 6/2014 | Snider et al. |
| 8,748,116 | B2 | 6/2014 | Lee |
| 8,871,452 | B2 | 6/2014 | Lee |
| 10,408,845 | B2 * | 9/2019 | Snider ........................ A61P 9/00 |
| 2005/0177196 | A1 | 8/2005 | Soykan et al. |
| 2007/0248981 | A1 | 10/2007 | Snider et al. |
| 2009/0092998 | A1 | 4/2009 | Dudley |
| 2009/0305265 | A1 | 12/2009 | Snider et al. |
| 2010/0009356 | A1 | 1/2010 | Snider et al. |
| 2010/0055683 | A1 | 3/2010 | Snider et al. |
| 2011/0053170 | A1 | 3/2011 | Snider et al. |
| 2011/0256635 | A1 | 10/2011 | Snider |
| 2012/0040381 | A1 | 2/2012 | Snider et al. |
| 2012/0065897 | A1 | 3/2012 | Snider et al. |
| 2013/0177931 | A1 | 7/2013 | Snider |
| 2013/0244236 | A1 | 9/2013 | Snider et al. |
| 2014/0045200 | A1 | 2/2014 | Snider et al. |
| 2014/0051773 | A1 | 2/2014 | Snider |
| 2014/0058743 | A1 | 2/2014 | Snider et al. |
| 2014/0234875 | A1 | 8/2014 | Snider |
| 2014/0286944 | A1 | 9/2014 | Snider et al. |
| 2014/0302536 | A1 | 10/2014 | Snider et al. |
| 2015/0081224 | A1 | 3/2015 | Snider et al. |

FOREIGN PATENT DOCUMENTS

| | | |
|---|---|---|
| CN | 101984766 | 3/2011 |
| EP | 2107377 | 10/2009 |
| JP | 2005-538700 | 12/2005 |
| JP | 2007-523324 | 8/2007 |
| JP | 2009-534691 | 9/2009 |
| JP | 2009-535649 | 10/2009 |
| JP | 2009-545735 | 12/2009 |
| JP | 2010-041998 | 2/2010 |
| JP | 2011-516846 | 5/2011 |
| JP | 2011-520098 | 7/2011 |
| WO | WO 2003/094856 | 11/2003 |
| WO | WO 2007/127749 | 11/2007 |
| WO | WO 2007/130962 | 11/2007 |
| WO | WO 2007/143295 | 12/2007 |
| WO | WO 2008/015254 | 2/2008 |
| WO | WO 2009/129454 | 10/2009 |
| WO | WO 2010/041046 | 4/2010 |
| WO | WO 2011/103330 | 8/2011 |
| WO | WO 2011/127412 | 10/2011 |

OTHER PUBLICATIONS

MX Office Action in Mexican Appln. No. MX/a/2018/009019, dated Feb. 12, 2021, 12 pages (with English translation).
CN Office Action in Chinese Appln. No. 201810869357.1, dated Jan. 22, 2021, 9 pages (with English translation).
Lv et al., "Correlation of sST2, BNP concentration and LVMI in patients with chronic heart failure," Chinese Journal of Clinical Rational Drug Use, Mar. 2012, 5(3), 2 pages (English Abstract).
Moss et al., "Cardiac-resynchronization therapy for the prevention of heart-failure events," New England Journal of Medicine, Oct. 1, 2009, 361(14):1329-38.
U.S. Appl. No. 14/290,465, Lee, filed May 29, 2014.
U.S. Appl. No. 14/523,694, Lee, filed Oct. 24, 2014.
U.S. Appl. No. 14/566,938, Snider et al., filed Dec. 11, 2014.
U.S. Appl. No. 14/566,955, Snider et al., filed Dec. 11, 2014.
U.S. Appl. No. 14/592,961, Snider et al., filed Jan. 9, 2015.
U.S. Appl. No. 29/503,093, Snider et al., filed Sep. 23, 2014.
U.S. Appl. No. 29/503,095, Snider et al., filed Sep. 23, 2014.
U.S. Appl. No. 29/503,097, Snider et al., filed Sep. 23, 2014.
AU Australian Office Action in Appln. No. 2013262515, dated Mar. 7, 2017, 4 pages.
CN Action in Chinese Patent Application No. 201380037345.8, dated Sep. 20, 2016.
CN Chinese Office Action in Appln. No. 201380037345.8, dated Jun. 2, 2017.
CN Office Action in Chinese Patent Appln. No. 201380037345.8, dated Jan. 27, 2016.
CN Office Action in Chinese Patent Appln. No. 201380037345.8, dated Dec. 6, 2017.
EP European Office Action in European Appln. No. 13790571.7, dated Oct. 23, 2017.
EP European Search Report in Appln. No. 18193293.0, dated Nov. 6, 2018, 7 pages.
EP Extended European Search Report in European Patent Appl. No. 13790571.7 dated Dec. 21, 2015.
IN Office Action in Indian Appln. No. 9776/DELNP/2014, dated Nov. 20, 2018, 6 pages (with English translation).
JP Office Action in Japanese Application No. 2015-512902, dated Mar. 23, 2017, 12 pages (with English translation).
JP Office Action in Japanese Appln. No. 2018-038175, dated Feb. 28, 2019, 8 pages (with English translation).
Ky et al., "High-sensitivity ST2 for prediction of adverse outcomes in chronic heart failure," *Circulation Heart Failure* 4(2):180-187, 2011.
Moss et al., "Cardiac-resynchronization therapy for the prevention of heart-failure events," *New Engl. J. Med.* 361(14):1329-1338, 2009.
MX Office Action in Mexican Appln. No. MX/a/2014/013995, dated Feb. 21, 2018, 6 pages (with English translation).
Pascual-Figal. D.A. et al., "Soluble ST2 for predication sudden cardiac death in patients with chronic heart failure and left ventricular systolic dysfunction." *J. Am. Coll. Cardiol.* 54(23):2174-9, 2009.
PCT International Preliminary Report on Patentability in International Appln. No. PCT/US2013/041686, dated Nov. 18, 2014.
PCT International Search Report and Written Opinion in International Appln. No. PCT/US2013/041686, dated Aug. 27, 2013, 16 pages.

(56) References Cited

OTHER PUBLICATIONS

Rehman, S.U. et al., "Characteristics of the novel interleukin family biomarker ST2 in patients with acute heart failure," *J. Am. Coll. Cardiol.* 52(18):1458-65, 2008.

Scott et al., "Defining potential to benefit from implantable cardioverter defibrillator therapy: the role of biomarkers," *Europace* 13:1419-1427, Jul. 2011.

Stolen et al., "Monitoring Arrhythmic Risk in Stable Heart Failure Patients with Soluble ST2," *Heart Failure*, pp. 1-4, May 2012.

Weinberg et al., "Identification of serum soluble ST2 receptor as a novel hear failure biomarker"; *Circulation* 107(5):721-6, 2003.

MX Office Action in Mexican Appln. No. MX/a/2018/009019, dated Aug. 10, 2021, 13 pages (with English translation).

\* cited by examiner

SEQUENCE LISTING

```
<160> NUMBER OF SEQ ID NOS: 1

<210> SEQ ID NO 1
<211> LENGTH: 327
<212> TYPE: PRT
<213> ORGANISM: Homo sapiens

<400> SEQUENCE: 1

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
```

```
            20                  25                  30
Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Glu Arg Asn Arg Val
 50                  55                  60

Phe Ala Ser Gly Gln Leu Leu Lys Phe Leu Pro Ala Ala Val Ala Asp
 65              70                  75                  80

Ser Gly Ile Tyr Thr Cys Ile Val Arg Ser Pro Thr Phe Asn Arg Thr
            85                  90                  95

Gly Tyr Ala Asn Val Thr Ile Tyr Lys Lys Gln Ser Asp Cys Asn Val
              100                 105                110

Pro Asp Tyr Leu Met Tyr Ser Thr Val Ser Gly Ser Glu Lys Asn Ser
            115                 120                 125

Lys Ile Tyr Cys Pro Thr Ile Asp Leu Tyr Asn Trp Thr Ala Pro Leu
            130                 135                 140

Glu Trp Phe Lys Asn Cys Gln Ala Leu Gln Gly Ser Arg Tyr Arg Ala
145                 150                 155                 160

His Lys Ser Phe Leu Val Ile Asp Asn Val Met Thr Glu Asp Ala Gly
                165                 170                 175

Asp Tyr Thr Cys Lys Phe Ile His Asn Glu Asn Gly Ala Asn Tyr Ser
            180                 185                 190

Val Thr Ala Thr Arg Ser Phe Thr Val Lys Asp Glu Gln Gly Phe Ser
            195                 200                 205

Leu Phe Pro Val Ile Gly Ala Pro Ala Gln Asn Glu Ile Lys Glu Val
        210                 215                 220

Glu Ile Gly Lys Asn Ala Asn Leu Thr Cys Ser Ala Cys Phe Gly Lys
225                 230                 235                 240

Gly Thr Gln Phe Leu Ala Ala Val Leu Trp Gln Leu Asn Gly Thr Lys
                245                 250                 255

Ile Thr Asp Phe Gly Glu Pro Arg Ile Gln Gln Glu Glu Gly Gln Asn
                260                 265                 270

Gln Ser Phe Ser Asn Gly Leu Ala Cys Leu Asp Met Val Leu Arg Ile
            275                 280                 285

Ala Asp Val Lys Glu Glu Asp Leu Leu Leu Gln Tyr Asp Cys Leu Ala
        290                 295                 300

Leu Asn Leu His Gly Leu Arg Arg His Thr Val Arg Leu Ser Arg Lys
305                 310                 315                 320

Asn Pro Ser Lys Glu Cys Phe
                325
```

METHODS FOR TREATING OR PREDICTING RISK OF A VENTRICULAR TACHYARRHYTHMIA EVENT

CROSS-REFERENCE TO RELATED APPLICATIONS

This application is a continuation application of U.S. patent application Ser. No. 15/370,049, filed on Dec. 6, 2016, which is a continuation application of U.S. patent application Ser. No. 13/897,249, filed on May 17, 2013, which claims the benefit of U.S. Provisional Patent Application Ser. No. 61/649,202, filed May 18, 2012, each of which are incorporated herein by reference in their entirety.

TECHNICAL FIELD

Provided herein are methods that include determining a level of soluble ST2 in a biological sample from a subject, comparing the level of soluble ST2 in the biological sample to a reference level of soluble ST2 (e.g., a level of soluble ST2 in the subject at an earlier time point), and selecting, implanting, replacing, or reprogramming an implanted cardiac device, e.g., an ICD, CRT, or CRT-D device, for a subject having an elevated level of soluble ST2 in the biological sample compared to the reference level of soluble ST2.

Also provided are methods for selecting a subject for participation in, or stratifying a subject participating in, a clinical study of a treatment for reducing the risk of a ventricular tachyarrhythmia (VTA) event and methods of evaluating the risk of a VTA event in a subject that include determining a level of soluble ST2 in a biological sample from the subject. Also provided are kits for performing any of these methods.

BACKGROUND OF THE INVENTION

Ventricular tachyarrhythmia (VTA) refers to a variety of medical conditions characterized by an abnormally elevated heart rate. When the heart beats excessively rapidly, the heart pumps less efficiently, and provides less blood flow to the rest of the body. The increased heart rate also leads to increased work and oxygen demand by the heart, which can lead to rate-related ischemia. Ventricular tachyarrhythmia events are related to sudden deaths, especially in patients with severe heart disease. Examples of ventricular tachyarrhythmia events include ventricular tachycardia, ventricular fibrillation, and ventricular flutter. Subjects diagnosed as having ventricular tachyarrhythmia often receive an implantable cardiac device, e.g., a cardiac defibrillator (ICD) or cardiac resynchronization treatment (CRT) device, or a combination ICD-CRT (CRT-D) device. Some subjects having ventricular tachyarrhythmia that receive such a device demonstrate reduced morbidity and mortality (Scott et al., Europace. 13(10):1419-27 (2011)). Some patients diagnosed with heart failure and receiving standard pharmacological therapy develop worsening disease, whereby such pharmacological therapy is no longer sufficient, and device therapy (e.g., ICD, CRT, or CRT-D device) becomes necessary to preserve these patients' lives. Existing guidelines for selecting treatment including an implanted cardiac device (see, e.g., Epstein et al., Circulation. 117:e350-e408 (2008)) are unable to predict which subjects will benefit most from device therapy.

SUMMARY

The invention is based, at least in part, on the discovery that subjects having an elevated level of soluble ST2 or an increase in soluble ST2 over time have an increased risk of having a ventricular tachyarrhythmia (VTA) event. Thus, provided herein are methods for selecting a treatment for a subject that include determining a level of soluble ST2 in a biological sample from a subject, comparing the level of soluble ST2 in the biological sample to a reference level of soluble ST2, and selecting an implanted cardiac device, e.g., an ICD, CRT, or CRT-D device, for a subject having a selected, e.g., elevated, level of soluble ST2 in the biological sample compared to the reference level of soluble ST2. Also provided are methods of treating a subject that include determining a level of soluble ST2 in a biological sample from a subject, comparing the level of soluble ST2 in the biological sample to a reference level of soluble ST2, and implanting a cardiac device into a subject having an elevated level of soluble ST2 in the biological sample compared to the reference level of soluble ST2; or altering the programming or replacing an existing device. Also provided are methods for selecting a subject for participation in, or stratification of subjects in, a clinical study of a treatment for reducing the risk of a VTA event, and methods of evaluating the risk of a VTA event in a subject that include determining a level of soluble ST2 in a biological sample from a subject. Also provided are kits that contain an antibody that specifically binds to soluble ST2 and instructions for performing any of the methods described herein. Also provided herein are methods of selecting a subject for treatment that include determining a level of soluble ST2 in a biological sample from a subject, comparing the level of soluble ST2 in the biological sample to a reference level of soluble ST2, and selecting a subject having an elevated level of soluble ST2 in the biological sample compared to the reference level of soluble ST2 for implantation of or treatment with a cardiac device, e.g., an ICD, CRT, or CRT-D device.

Provided herein are methods for selecting a treatment for or treating a subject that include determining a level of soluble ST2 in a biological sample from a subject, comparing the level of soluble ST2 in the biological sample to a reference level of soluble ST2, and selecting, implanting, replacing, or reprogramming an implanted cardiac device for a subject based on levels of soluble ST2 in the biological sample as compared to the reference level of soluble ST2. In some embodiments, the subject has heart failure or the subject has previously had at least one VTA event; in some embodiments, the subject has a cardiac device implanted. In some embodiments, the reference level of soluble ST2 is a level of soluble ST2 in healthy subject. In some embodiments, the biological sample contains blood, serum, or plasma. Also provided are methods of selecting a subject for treatment that include determining a level of soluble ST2 in a biological sample from a subject, comparing the level of soluble ST2 in the biological sample to a reference level of soluble ST2, and selecting a subject having an elevated level of soluble ST2 in the biological sample to the reference level of soluble ST2 for implantation of or treatment with a cardiac device, e.g., an ICD, CRT, or CRT-D device.

Some embodiments further include determining the level of one of more additional biomarkers selected from the group consisting of: atrial natriuretic peptide (ANP), proANP, N-terminal (NT)-proANP, brain natriuretic peptide (BNP), proBNP, NT-proBNP, cardiac troponin I, C-reactive protein, creatinine, endothelin-1, and Blood Urea Nitrogen (BUN) in the biological sample, comparing the level of the one or more additional biomarkers in the biological sample to a reference level of the one of more additional biomarkers, and selecting, implanting, replacing, or reprogramming an implanted cardiac device for a subject having an elevated level of the one or more additional biomarkers in the biological sample compared to the reference level of the one or more additional biomarkers. In some embodiments, the one or more additional biomarkers are selected from the group consisting of BNP, proBNP, and NT-proBNP.

Also provided are methods of selecting a treatment for or treating a subject that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and selecting, implanting, replacing, or reprogramming an implanted cardiac device for a subject having an elevated level of soluble ST2 in the second biological sample compared to the level of soluble ST2 in the first biological sample. In some embodiments, the subject has heart failure or the subject has previously had at least one VTA event. In some embodiments, the first time point and the second time point are within one year of each other. In some embodiments, the biological sample contains blood, serum, or plasma.

Some embodiments further include determining the level of one of more additional biomarkers selected from the group consisting of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in the first and/or second biological sample, comparing the levels of the one or more additional biomarkers in the first and/or second biological sample to a reference level of the one of more additional biomarkers, and selecting, implanting, replacing, or reprogramming an implanted cardiac device for a subject having an elevated level of the one or more additional biomarkers in the first and/or second biological sample compared to the reference level(s) of the one or more additional biomarkers. In some embodiments, the one or more additional biomarkers are selected from the group consisting of BNP, proBNP, and NT-proBNP.

Also provided are methods of treating a subject that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and implanting an ICD or a CRT device into a subject having an elevated level of soluble ST2 in the second biological sample compared to the level of soluble ST2 in the first biological sample. Also provided are methods of selecting a treatment for a subject that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and selecting a treatment that includes the implantation of an ICD or a CRT device for a subject having an elevated level of soluble ST2 in the second biological sample compared to the level of soluble ST2 in the first biological sample. In some embodiments, the subject has heart failure or the subject has previously had at least one VTA event. In some embodiments, the first time point and the second time point are within one year of each other. In some embodiments, the first and second biological samples contain blood, serum, or plasma.

Some embodiments further include determining the level of one of more additional biomarkers selected from the group of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in the first and/or second biological sample, comparing the level of the one or more additional biomarkers in the first and/or second biological sample to a reference level of the one of more additional biomarkers, and implanting a cardiac device into a subject having an elevated level of the one or more additional biomarkers in the first and/or second biological sample compared to the reference level of the one or more additional biomarkers. In some embodiments, the one or more additional biomarkers are selected from the group of BNP, proBNP, and NT-proBNP.

In some embodiments, the methods include determining a level or ratio of ST2, and a level or ratio of BNP, proBNP, or NT-proBNP, comparing the levels or ratios of ST2 and BNP, proBNP, or NT-proBNP to reference levels or ratios, and selecting, implanting, replacing, or reprogramming an implanted cardiac device based on the results of the comparison.

Also provided are methods of selecting a subject for participation in, or stratifying subjects in, a clinical study of a treatment for reducing the risk of a VTA event that include determining a level of soluble ST2 in a biological sample from a subject, comparing the level of soluble ST2 in the biological sample to a reference level of soluble ST2, and selecting a subject having an elevated level of soluble ST2 in the biological sample compared to the reference level of soluble ST2 for participation in, or stratifying a subject based on the level of soluble ST2 in the biological sample, in a clinical trial of a treatment for reducing the risk of a VTA event. In some embodiments, the subject has heart failure or the subject has previously had at least one VTA event. In some embodiments, the reference level of soluble ST2 is a level of soluble ST2 in a healthy subject. In some embodiments, the biological sample contains blood, serum, or plasma.

Some embodiments further include determining the level of one of more additional biomarkers selected from the group of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in the biological sample, comparing the level of the one or more additional biomarkers in the biological sample to a reference level of the one of more additional biomarkers, and selecting a subject having an elevated level of the one or more additional biomarkers in the biological sample compared to the reference level of the one or more additional biomarkers for participation in, or stratifying a subject based on the level of the one or more additional biomarkers in the biological sample, in a clinical trial of a treatment for reducing the risk of a VTA event. In some embodiments, the one or more additional biomarkers are selected from the group of BNP, proBNP, and NT-proBNP.

Also provided herein are methods for selecting a subject for participation in, or stratifying subjects in, a clinical study of a treatment for reducing the risk of a ventricular tachyarrhythmia (VTA) event that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and selecting a subject having an elevated level of soluble ST2 in the second biological sample compared to the level of soluble ST2 in the first biological sample for participation in, or stratifying a subject based on the level of soluble ST2 in the first and/or second biological sample, in a clinical trial of a treatment for reducing the risk of a VTA event. In some embodiments, the subject has heart failure or the subject has previously had at least one VTA event. In some embodiments, the first time point and the second time point are within one year of each other. In some embodiments, the first and second biological samples are or contain blood, serum, or plasma.

Some embodiments further include determining the level of one of more additional biomarkers selected from the group of: atrial natriuretic peptide (ANP), proANP, N-terminal (NT)-proANP, brain natriuretic peptide (BNP), proBNP, NT-proBNP, cardiac troponin I, C-reactive protein, creatinine, endothelin-1, and Blood Urea Nitrogen (BUN) in the first and/or second biological sample, comparing the level of the one or more additional biomarkers in the first and/or second sample to a reference level of the one of more additional biomarkers, and selecting a subject having an elevated level of the one or more additional biomarkers in the first and/or second biological sample compared to the reference level of the one or more additional biomarkers for participation in, or stratifying a subject based on the level of the one or more additional biomarkers in the first and/or second biological sample, in a clinical trial of a treatment for reducing the risk of a VTA event. In some embodiments, the one or more additional biomarkers are selected from the group consisting of BNP, proBNP, and NT-proBNP.

Also provided are methods for evaluating the risk of a ventricular tachyarrhythmia (VTA) event in a subject that include determining a level of soluble ST2 in a biological sample from a subject, comparing the level of soluble ST2 in the biological sample to a reference level of soluble ST2; and identifying a subject having an elevated level of soluble ST2 in the biological sample compared to the reference level of soluble ST2 as having an increased risk of a VTA event, optionally the methods include identifying a subject having no significant change or a decreased level of soluble ST2 in the biological sample compared to the reference level of soluble ST2 as having a decreased risk of a VTA event. In some embodiments, the VTA event is ventricular tachycardia, ventricular fibrillation, or ventricular flutter. In some embodiments, the subject has heart failure or the subject has an implanted cardiac device. In some embodiments, the reference level of soluble ST2 is a level of soluble ST2 in a healthy subject, e.g., a subject who has substantially the same risk of a VTA event as a subject who does not have heart failure. In some embodiments, the risk of a VTA event is the risk of a VTA event within one year, 90 days, 60 days, or 30 days. In some embodiments, the biological sample is or contains blood, serum, or plasma.

Some embodiments further include determining the level of one of more additional biomarkers selected from the group of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in the biological sample, comparing the level of the one or more additional biomarkers in the biological sample to a reference level of the one or more additional biomarkers, and identifying a subject having an elevated level of the one or more additional biomarkers in the biological sample compared to the reference level of the one or more additional biomarkers as having an increased risk of the condition with which the biomarker is associated and/or an increased risk of a VTA event. In some embodiments, the one or more additional biomarkers are selected from the group consisting of BNP, proBNP, and NT-proBNP.

Also provided are methods for evaluating the risk of a ventricular tachyarrhythmia (VTA) event in a subject that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and identifying a subject having an elevated level of soluble ST2 in the second biological sample compared to the level of soluble ST2 in the first biological sample as having an increased risk of a VTA event. In some embodiments, the VTA event is ventricular tachycardia, ventricular fibrillation, or ventricular flutter. In some embodiments, the subject has heart failure or has an implanted cardiac device. In some embodiments, the risk of a VTA event is the risk of a VTA event within one year. In some embodiments, the first time point and the second time point are within one year of each other. In some embodiments, the first and second biological samples comprise blood, serum, or plasma.

Some embodiments further include determining the level of one of more additional biomarkers selected from the group of: atrial natriuretic peptide (ANP), proANP, N-terminal (NT)-proANP, brain natriuretic peptide (BNP), proBNP, NT-proBNP, cardiac troponin I, C-reactive protein, creatinine, and Blood Urea Nitrogen (BUN) in the first and/or second biological sample, comparing the level of the one or more additional biomarkers in the first and/or second sample to a reference level of the one or more additional biomarkers, and identifying a subject having an elevated level of the one or more additional biomarkers in the first and/or second biological sample compared to the reference level of the one or more additional biomarkers as having an increased risk of the condition with which the biomarker is associated and/or an increased risk of a VTA event. In some embodiments, the one or more additional biomarkers is BNP, proBNP, or NT-proBNP.

In some embodiments of all of the methods described herein, where two levels of an additional biomarker are measured, the first and second level are compared and the presence of an increase in the biomarker from the first to the second level indicates an increased risk of the condition with which the biomarker is associated.

In some embodiments of any of the above aspects, the subject is human.

Also provided are kits containing an antibody that specifically binds to soluble ST2; and instructions for performing any of the methods described herein.

By the term "ventricular tachyaryrrthmia event" or "VTA" is meant a medical condition that is characterized by an abnormal, increased heart rate. In some embodiments, the abnormal, increased heart rate originates in one of the ventricles of the heart. Non-limiting examples of VTA events include ventricular tachycardia (e.g., life-threatening ventricular tachycardia), ventricular fibrillation (e.g., life-threatening ventricular fibrillation), and ventricular flutter (e.g., life-threatening ventricular flutter).

By the term "implanted cardiac device" or "cardiac device" is meant a medical device used to treat subjects who have arrhythmia, e.g., who are at risk of sudden cardiac death. Implanted cardiac devices include cardiac resynchronization therapy (CRT) devices, implantable cardioverter defibrillator (ICD) devices, and cardiac resynchronization therapy defibrillator (CRT-D) devices.

By the term "implanted cardiac defibrillator device" or "ICD device" is meant a small electrical impulse generating medical device that is implanted in subjects determined to be at risk of having a future VTA event. An ICD is programmed to detect the onset of a VTA event and stabilize or reset the heart rate of the subject, e.g., by anti-tachycardia pacing (ATP) or by delivering an electrical pulse to the subject, e.g., shocking the heart when it is beating too fast to prevent cardiac arrest.

By the term "cardiac resynchronization therapy device" or "CRT device" is meant a small electrical biventricular pacing medical device with at least one lead (e.g., three leads to the right atrium, right ventricle, and left ventricle) that synchronizes the pumping of the heart that is implanted in subjects determined to be at risk of having a future VTA event. These pacemakers help a very slow heart beat more regularly.

By the term "cardiac resynchronization therapy defibrillator (CRT-D) device" is meant a device that functions both as a CRT device and an ICD device.

By the term "soluble ST2" is meant a soluble protein containing a sequence at least 90% identical (e.g., at least 95%, 96%, 97%, 98%, 99%, or 100% identical) to NCBI Accession No. NP_003847.2 (SEQ ID NO: 1) or containing a sequence at least 90% identical (e.g., at least 95%, 96%, 97%, 98%, 99%, or 100% identical) to amino acids 19-328 of SEQ ID NO: 1, or a nucleic acid containing a sequence at least 90% identical (e.g., at least 95%, 96%, 97%, 98%, 99%, or 100% identical) to NCBI Accession No. NM_003856.2 or containing a sequence at least 90% identical (e.g., at least 95%, 96%, 97%, 98%, 99%, or 100% identical) to nucleotides 285 to 1214 of NCBI Accession No. NM_003856.2.

By the term "elevated" or "elevation" is meant a difference, e.g., a statistically significant or detectable increase in a determined or measured level (e.g., a human soluble ST2 protein level) compared to a reference level (e.g., a level of human soluble ST2 in a subject not having a disease, a subject not presenting with two or more symptoms of a disease, or a subject not identified as being at risk of developing a disease, or a threshold level of human soluble ST2). In some embodiments, the reference is a threshold level, and any level above that is considered "elevated." Additional reference levels of human soluble ST2 are described herein and are known in the art.

As used herein, a "biological sample" includes one or more of blood, serum, plasma, urine, and body tissue. Generally, a biological sample is a sample containing serum, blood, or plasma.

By the term "health care facility" is meant a location were a subject may receive medical care or treatment from a health care professional (e.g., a nurse, a physician, or a physician's assistant). Non-limiting examples of health care facilities include hospitals, clinics, surgical centers, and assisted care facilities (e.g., a nursing home).

By the term "reference level" is meant a threshold level or a level in a control subject or control patient population. A reference level will depend on the assay performed and can be determined by one of ordinary skill in the art. A reference level may be a baseline level or a level in the same patient measured at an earlier point in time. In some embodiments, a reference level is a level of soluble ST2 in a control subject that does not have a cardiovascular disorder (e.g., arrhythmia, cardiomyopathy, coronary artery disease, myocardial infarction, or heart failure). In some embodiments, a reference level is a level of soluble ST2 in a healthy subject. Additional examples of reference levels of soluble ST2 are known in the art and are described herein.

In some embodiments, a ratio of two soluble ST2 levels in a subject is determined and compared to a reference ratio (e.g., a ratio of soluble ST2 levels measured in a control subject (e.g., any of the control subjects described herein or the same subject at earlier time points). Additional examples of reference ratios of soluble ST2 are known in the art and are described herein.

As used herein, a "subject" is a mammal, e.g., a human. In all embodiments, human nucleic acids, human polypeptides, and human subjects can be used.

By the term "healthy subject" is meant a subject that has not had a VTA event or is not at risk of having a VTA event (e.g., any of the VTA events described herein). For example, a healthy subject has not had a VTA event, is not at risk of having a VTA event, and has not experienced two or more (e.g., two, three, four, or five) symptoms of a VTA event. In some embodiments, a healthy subject has not had a VTA event, is not at risk of having a VTA event, and does not present with two or more symptoms of a disease state.

By the term "disease state" is meant the manifestation of one or more (e.g., at least two, three, four, or five) symptoms in a subject that indicate either an abnormal decrease in the viability and/or an abnormal decrease/malfunction of a biological activity of one or more (e.g., at least two, three, four, or five) tissues in the body of the subject. Non-limiting examples of disease states in a subject include a cardiac disease (e.g., arrhythmia, heart failure, heart attack, coronary artery disease, cardiovascular disease, acute coronary syndrome, and angina), inflammation, stroke, renal failure, obesity, high cholesterol, and dyslipidemia.

By the phrase "physical symptoms associated with a disease state" is meant the one or more (e.g., at least two, three, or four) symptoms that are manifested by a subject having a particular disease state. Physical symptoms associated with several disease states are known in the art by medical health professionals (e.g., physicians). Non-limiting examples of physical symptoms associated with a cardiac disease (e.g., arrhythmia, heart failure, coronary artery disease, cardiovascular disease, acute coronary syndrome, and angina) include shortness of breath, heart palpitations, increased heart rate, weakness, dizziness, nausea, sweating, chest discomfort or pressure, chest pain, arm pain, chronic fullness, indigestion, sweating, wheezing, sleep apnea, and anxiety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
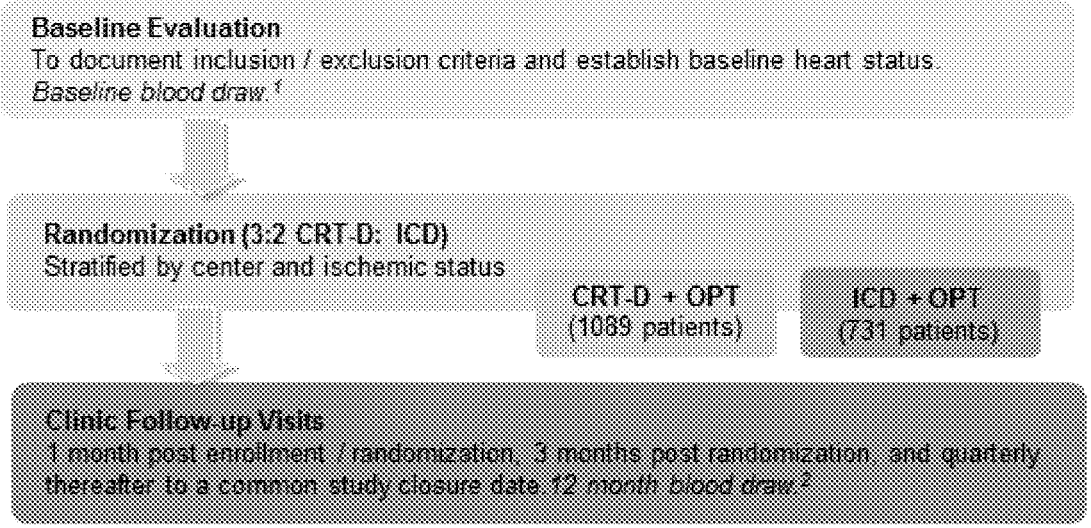
FIG. 1 is a schematic showing the design of the MADIT-CRT clinical study.

As described herein, subjects having an elevated level of soluble ST2 or an increase in soluble ST2 over time have an increased risk of having a ventricular tachyarrhythmia (VTA) event. Thus, provided herein are methods for selecting a treatment for or treating a subject that include determining a level of soluble ST2 in a biological sample from a subject, comparing the level of soluble ST2 in the biological sample to a reference level of soluble ST2, and selecting, implanting, replacing, or reprogramming an implanted cardiac device, e.g., an ICD, CRT, or CRT-D device, for a subject having an elevated level of soluble ST2 in the biological sample compared to the reference level of soluble ST2. Also provided are methods for selecting a subject for participation in, or stratifying subjects in, a clinical study of a treatment for reducing the risk of a VTA event, and methods of evaluating the risk of a VTA event in a subject that include determining a level of soluble ST2 in a biological sample from a subject. Also provided are kits that contain at least one antibody that specifically binds to soluble ST2 for use in the methods described herein, and optionally instructions for performing any of the methods described herein.

ST2

The ST2 gene, also known as interleukin 1 receptor-like 1 (IL1RL1) is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe heart failure (Weinberg et al., Circulation 107(5):721-6 (2003)), as well in subjects with acute myocardial infarction (MI) (Shimpo et al., Circulation 109(18):2186-90 (2004)).

The transmembrane form of ST2 is thought to play a role in modulating responses of T-helper type 2 cells (Lohning et al., Proc. Natl. Acad. Sci. U.S.A. 95(12):6930-6935 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2 (IL1RL1), which is a soluble secreted form; and ST2L, a transmembrane receptor form that is very similar to the interleukin-1 receptors. The HUGO Nomenclature Committee designated the human homolog of ST2, the cloning of which was described in Tominaga et al., Biochim. Biophys. Acta. 1171: 215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2 (SEQ ID NO: 1; shown below). The mRNA sequence for the longer form of human ST2 is at GenBank Acc. No. NM_016232.4; and the polypeptide sequence is at GenBank Acc. No. NP_057316.3. Additional information is available in the public databases at GeneID: 9173, MIM ID # 601203, and UniGene No. Hs.66. In general, in the methods described herein, the soluble form of ST2 polypeptide is measured. Non-limiting examples of soluble ST2 protein include proteins containing a sequence at least 90% identical (e.g., at least 95%, 96%, 97%, 98%, 99%, or 100% identical) to the sequence of SEQ ID NO: 1. Non-limiting examples of soluble ST2 nucleic acids include nucleic acids containing a sequence at least 90% identical (e.g., at least 95%, 96%, 97%, 98%, 99%, or 100% identical) to the sequence of NCBI Accession No. NM_003856.2

```
Human Soluble ST2 Protein
                                                              (SEQ ID NO: 1)
  1 mgfwilailt ilmystaakf skqswglene alivrcprqg kpsytvdwyy sqtnksipt 61 ernrvfasgq llkflpaava dsgiytcivr sptfnrtgya nvtiykkqsd cnvpdylmys 121 tvsgseknsk iycptidlyn wtaplewfkn cqalqgsryr ahksflvidn vmtedagdyt 181 ckfihnenga nysvtatrsf tvkdeqgfsl fpvigapaqn eikeveigkn anltcsacfg 241 kgtqflaavl wqlngtkitd fgepriqqee gqnqsfsngl acldmvlria dvkeedlllq 301 ydclalnlhg lrrhtvrlsr knpskecf
```

Methods for detecting and measuring soluble ST2 are known in the art, e.g., as described in U.S. Patent Application Publication Nos. 2003/0124624, 2004/0048286, and 2005/0130136, the entire contents of each of which are incorporated herein by reference. In some embodiments, the methods include determining the identity of the nucleotide sequence at RefSNP ID: rs1041973.

Kits for measuring soluble ST2 polypeptide are also commercially available, e.g., the ST2 ELISA Kit manufactured by Medical & Biological Laboratories Co., Ltd. (MBL International Corp., Woburn, Mass.), No. 7638, and the Presage® ST2 Assay, Critical Care Diagnostics, San Diego, Calif. In addition, devices for measuring soluble ST2 and other biomarkers are described in U.S. Patent Publication No. 2005/0250156. Levels of soluble ST2 protein can also be measured using the antibodies produced from the hybridoma deposited at American Type Culture Collection and designated by Patent Deposit Designation PTA-10432, and those antibodies described in U.S. Patent Application Publication No. 2011/0256635 and WO 2011/127412 (each of which is herein incorporated by reference).

In some embodiments, the level of soluble ST2 is determined more than once; in some embodiments, the higher measurement can be used. In embodiments where the level of soluble ST2 is determined more than once, the highest level can be used, or the change in levels (e.g., a ratio of two levels of ST2) can be determined and used.

Levels of soluble ST2 can also be determined multiple times to evaluate a subject's response to a treatment for reducing the risk of a VTA event (e.g., a CRT or ICD). For example, a level of soluble ST2 taken after implantation of an ICD or CRT, can be compared to levels of soluble ST2 before implantation of an ICD or CRT, e.g., a baseline level. The change in soluble ST2 levels would indicate whether the implantation of an ICD or CRT was effective; e.g., a reduction in soluble ST2 level over time would indicate that the implantation of an ICD or CRT was effective. Other exemplary methods that include determining a level of soluble ST2 (e.g., one or more levels of soluble ST2) are described herein.

ST2 Reference Levels

Once a level of soluble ST2 has been determined in a biological sample from a subject, the level may be compared to a reference level (e.g., any of the reference levels described herein or known in the art). In some embodiments, e.g., where the level of soluble ST2 is determined using an ELISA, the reference level may represent a threshold level, above which the subject is identified as having an increased risk of an VTA event (and optionally selected for implantation with an implanted cardiac device, e.g., an ICD, CRT, or CRT-D device, or selected for participation in a clinical study of a treatment for preventing or reducing the risk of a VTA event). The reference level chosen may depend on the methodology (e.g., the particular antibody or ELISA kit) used to measure the levels of soluble ST2. Reference levels of soluble ST2 are known in the art and may readily be determined by one skilled in the art.

Non-limiting threshold levels of soluble ST2 may represent a level, e.g., a median, quartile, tertile, or other cutoff level, of soluble ST2 in particular patient populations, e.g., subjects with a BMI of less than 25, subjects with normal renal function, subjects without a cardiac disease (e.g., any of the cardiac diseases described herein), and healthy (e.g., undiagnosed with disease, having a low risk of developing disease, and not presenting with two or more symptoms of a disease) men, women, or children. For example, a threshold value for soluble ST2 may fall within the range of about 1.0 to 10 ng/mL, 5.0 ng/mL to 10 ng/mL, about 10.0 ng/mL to 20.0 ng/mL, about 10.0 ng/mL to 15.0 ng/mL, about 15.0 ng/mL to 20.0 ng/mL, about 20.0 ng/ml to 40 ng/mL, about 20 ng/mL to 30 ng/mL, about 20 ng/mL to 25 ng/mL, about 25 ng/mL to 30 ng/mL, about 30 ng/mL to about 40 ng/mL, about 30 ng/mL to 35 ng/mL, about 35 ng/mL to 40 ng/mL, about 40 ng/mL to about 60 ng/mL, about 40 ng/mL to about 50 ng/mL, and about 50 ng/mL to about 60 ng/mL. Additional threshold values for soluble ST2 may fall within the range of about 10 pg/mL to about 50 pg/mL, about 15 pg/mL to about 45 pg/mL, about 15 pg/mL to about 40 pg/mL, about 20 pg/mL to about 45 pg/mL, about 25 pg/mL to about 45 pg/mL, about 30 pg/mL to about 40 pg/mL, or about 35 pg/mL.

In some embodiments, the threshold value for soluble ST2 in men and women may be any value listed in the Table 1. For example, the threshold value of soluble ST2 in men may be between 17.0 ng/mL to 19.0 ng/mL, 19.0 ng/mL to 21.0 ng/mL, 21.0 ng/mL to 23.0 ng/mL, 23.0 ng/mL to 25.0 ng/mL, 25.0 ng/mL to 27.0 ng/mL, 27.0 ng/mL to 29.0 ng/mL, 29.0 ng/mL to 31.0 ng/mL, 31.0 ng/mL to 33.0 ng/mL, 33.0 ng/mL to 35.0 ng/mL, 35.0 ng/mL to 37.0 ng/mL, 37.0 ng/mL to 39.0 ng/mL, 39.0 ng/mL to 41.0 ng/mL, 41.0 ng/mL to 43.0 ng/mL, 43.0 ng/mL to 45.0 ng/mL, 45.0 ng/mL to 47.0 ng/mL, 47.0 ng/mL to 49.0 ng/mL, and 49.0 ng/mL to 51.0 ng/mL. Exemplary threshold values of soluble ST2 in women may be 12.0 ng/mL to 14.0 ng/mL, 14.0 ng/mL to 16.0 ng/mL, 16.0 ng/mL to 18.0 ng/mL, 18.0 ng/mL to 20.0 ng/mL, 20.0 ng/mL to 22.0 ng/mL, 22.0 ng/mL to 24.0 ng/mL, 24.0 ng/mL to 26.0 ng/mL, 26.0 ng/mL to 28.0 ng/mL, 28.0 ng/mL to 30.0 ng/mL, 30.0 ng/mL to 32.0 ng/mL, 32.0 ng/mL to 34.0 ng/mL, 34.0 ng/mL to 36.0 ng/mL, 36.0 ng/mL to 38.0 ng/mL, and 38.0 ng/mL to 40.0 ng/mL.

TABLE 1

Serum ST2 Concentrations in Males and Females

| Percentiles | ST2 (ng/mL) | | |
| --- | --- | --- | --- |
| | Combined | Male | Female |
| 2.5 | 8.0 | 8.6 | 7.3 |
| 25 | 14.5 | 17.6 | 12.4 |
| 50 | 18.8 | 23.6 | 16.2 |
| 75 | 25.3 | 30.6 | 19.9 |
| 90 | 34.3 | 37.2 | 23.7 |
| 95 | 37.9 | 45.4 | 29.0 |
| 97.5 | 45.6 | 48.5 | 33.1 |
| 99 | 50.2 | 52.7 | 39.9 |

As noted above, a threshold level of soluble ST2 may vary depending on the methodology used to measure the levels of soluble ST2. For example, if an antibody produced from the hybridoma deposited at American Type Culture Collection, designated with Patent Deposit Deposition PTA-10432, is used to determine a soluble ST2 level, non-limiting threshold values of soluble ST2 may include: below 20 ng/mL, 5 ng/mL to 15 ng/mL, 5.0 ng/mL to 10 ng/mL, 10 ng/mL to 20 ng/mL, 10 ng/mL to 15 ng/mL, 14.5 ng/mL to 25.3 ng/mL, 15 ng/mL to 25 ng/mL, 15 ng/mL to 20 ng/mL, 18.0 ng/mL to 20.0 ng/mL, 18.1 ng/mL to 19.9 ng/mL, 20 ng/mL to 30 ng/mL, 20 ng/mL to 25 ng/mL, 25 ng/mL to 35 ng/mL, 25 ng/mL to 30 ng/mL, 30 ng/mL to 40 ng/mL, 30 ng/mL to 35 ng/mL, 35 ng/mL to 45 ng/mL, 35 ng/mL to 40 ng/ml, and 40 ng/mL to 45 ng/mL. Additional soluble ST2 reference values that may be used, when the antibody produced from the hybridoma designated PTA-10432 is used to determine a soluble ST2 level, include: for women, 12.4 ng/mL to 19.9 ng/mL, 12.0 ng/mL to 20 ng/mL, 15.3 ng/mL to 17.4 ng/mL, 15.0 to 17.0 ng/mL, below 20 ng/mL, and below 18 ng/mL; and for men, less than 31.0 ng/mL, less than 26.0 ng/mL, 17.6 ng/mL to 30.6 ng/mL, 17.0 ng/mL to 30.0 ng/mL, 21.3 ng/mL to 25.1 ng/mL, and 21.0 ng/mL to 25.0 ng/mL. Additional non-limiting threshold values that may be used, when a soluble ST2 level is measured using the antibody produced from the hybridoma designated PTA-10432, include: 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, or 31 ng/mL.

In additional non-limiting examples, when a soluble ST2 level is measured using the ST2 ELISA Kit (MBL International Corp., Woburn, Mass.), the threshold levels of soluble ST2 include: 0.1 ng/mL to 0.6 ng/mL, 0.2 ng/mL to 0.6 ng/mL, 0.2 ng/mL to 0.5 ng/mL, 0.3 ng/mL to 0.5 ng/mL, 0.2 ng/mL to 0.3 ng/mL, 0.3 ng/mL to 0.4 ng/mL, and 0.4 ng/mL to 0.5 ng/mL. Additional non-limiting threshold values that may be used, when the ST2 ELISA Kit (MBL International Corp.) is used to measure a soluble ST2 level, include: 0.17 ng/mL, 0.18 ng/mL, 0.19 ng/mL, 0.20 ng/mL, 0.21 ng/mL, 0.22 ng/mL, 0.23 ng/mL, 0.24 ng/mL, 0.25 ng/mL, 0.26 ng/mL, 0.27 ng/mL, 0.28 ng/mL, or 0.29 ng/mL of blood, serum, or plasma.

In some embodiments, the reference level of soluble ST2 is a level of soluble ST2 present in a healthy subject (e.g., a subject that does not have a disease (e.g., cardiovascular disease), has not been diagnosed as having a disease, and/or is not presenting with two or more (e.g., two, three, four, or five) symptoms of a disease state). In some embodiments, a reference level of soluble ST2 is a level of soluble ST2 from the same subject at an earlier point in time. In some embodiments, the reference level of soluble ST2 is a level of soluble ST2 from a subject that does not have a cardiac disease, has not been diagnosed as having a cardiac disease, and/or does not have two or more symptoms associated with a cardiac disease (e.g., any of the cardiac diseases described herein or known in the art, e.g., arrhythmia, heart failure, heart attack, coronary artery disease, cardiovascular disease, acute coronary syndrome, and angina). In some embodiments, the reference level of soluble ST2 is a level of soluble ST2 from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina). In some embodiments, the control subject has not been diagnosed as having a cardiac disease, is not at risk of developing a cardiac disease, has a body mass index of less than 25, and has a cholesterol (total cholesterol, high density lipoprotein, and/or low density lipoprotein), and triglyceride profile within a normal range.

In some embodiments, the ratio of two soluble ST2 levels in a subject is compared to a reference ratio of soluble ST2 levels. In some embodiments, the reference ratio of soluble ST2 levels can be a threshold ratio (e.g., a reference ratio of soluble ST2 of 1.00, 1.01, 1.02, 1.03, 1.04, 1.05, 1.06, 1.07, 1.071, 1.08, 1.09, or 1.10). In some embodiments, the reference ratio of soluble ST2 is a ratio of two levels of soluble ST2 measured in a control subject (e.g., any of the control subjects described herein or the same subject). For example, a reference ratio can be a ratio of the levels of soluble ST2 collected at two different time points in a healthy subject (e.g., a subject that does not have a disease (e.g., any of the cardiac diseases described herein), has not been diagnosed as having a disease, and/or is not presenting with two or more (e.g., two, three, four, or five) symptoms of a disease state). In some embodiments, a reference ratio of soluble ST2 is a ratio of soluble ST2 levels from the same subject at an earlier point in time. In some embodiments, the reference ratio of soluble ST2 is a ratio of soluble ST2 levels from a subject that does not have a cardiac disease, has not been diagnosed as having a cardiac disease, and/or does not have two or more symptoms associated with a cardiac disease (e.g., arrhythmia, heart failure, heart attack, coronary artery disease, cardiovascular disease, acute coronary syndrome, and angina), inflammation, stroke, renal failure, obesity, high cholesterol, and dyslipidemia. In some embodiments, the reference ratio of soluble ST2 is a ratio of soluble ST2 levels from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina). In some embodiments, the reference ratio of soluble ST2 is a ratio of soluble ST2 levels from a subject that has not been diagnosed as having a cardiac disease, inflammation, stroke, renal failure, obesity, high cholesterol, and dyslipidemia.

Additional Markers

Some embodiments of all of the methods described herein, may further include determining the level of one or more (e.g., at least two, three, four, or four) additional markers in a biological sample from the subject, to provide further information regarding risk of a VTA (see, e.g., Scott et al., Europace. 13(10):1419-27 (2011) and references cited therein). The additional markers may be selected from the group of: proANP, NT-proANP, ANP, proBNP, NT-proBNP, BNP, troponin, CRP, creatinine, Blood Urea Nitrogen (BUN), galectin, liver function enzymes, albumin, endothelin-1, and bacterial endotoxin. The one or more additional markers can be measured in any of the biological samples herein. The presence of an elevated level (e.g., at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290%, or 300%) of one or more (e.g., at least two, three, or four) of proANP, NT-proANP, ANP, proBNP, NT-proBNP, BNP, troponin, CRP, creatinine, Blood Urea Nitrogen (BUN), galectin, liver function enzymes, albumin, endothelin-1, and bacterial endotoxin in a subject compared to a reference level for each of these additional biomarkers may further indicate that the subject has an increased risk of VTA, the subject should receive continued treatment (e.g., treatment on an inpatient basis), the subject should receive an ICD or CRT, the subject should be selected for implantation of an ICD or CRT, or the subject should be selected for participation in a clinical study of a treatment to decrease the risk of a VTA event.

In some embodiments, the level of one or more additional biomarkers is determined more than once; in some embodiments, the higher measurement can be used of an additional biomarker can be used. In embodiments where the level of an additional biomarker is determined more than once, the highest level can be used, or the change in levels (e.g., a ratio of two levels of an additional biomarker) can be determined and used.

Levels of an additional biomarker can also be determined multiple times to evaluate a subject's response to a treatment (e.g., a cardiac device). For example, a level of one or more additional biomarkers taken after implantation of a cardiac device, can be compared to levels of the one or more additional biomarkers before implantation of a cardiac device, e.g., a baseline level. The change in the level of one or more additional biomarkers would indicate or further indicate whether the implantation of a cardiac device was effective; e.g., a reduction in the level of one or more additional biomarkers would indicate or further indicate that the implantation of a cardiac device was effective. Other exemplary methods that include determining a level of one or more additional biomarkers (e.g., one or more levels of BNP, proBNP, and NT-proBNP) are described herein.

Once a level of an additional biomarker has been determined in a biological sample from a subject, the level may be compared to a reference level of the additional biomarker (e.g., any of the reference levels described herein or known in the art). In some embodiments, e.g., where the level of an additional biomarker is determined using an ELISA, the reference level may represent a threshold level, above which the subject is identified as having an increased risk of a disease associated with the biomarker, e.g., cardiovascular disease, and/or a VTA event. Such subjects can, for example, optionally selected for implantation, reprogramming, or replacement of a cardiac device, treated with implantation, reprogramming, or replacement of a cardiac device, or selected for participation in or stratified within a clinical study of a treatment for preventing a VTA event. The reference level of the additional biomarker chosen may depend on the methodology (e.g., the particular antibody or ELISA kit) used to measure the levels of the additional biomarker. Reference levels of additional biomarkers are known in the art and may readily be determined by one skilled in the art.

Non-limiting threshold levels of additional biomarkers may represent a threshold or cutoff level, e.g., a quartile, tertile, or median level of an additional biomarker in particular patient populations, e.g., subjects with a BMI of less than 25, subjects with normal renal function, subjects without cardiac disease (e.g., any of the cardiac diseases described herein), healthy (e.g., undiagnosed with disease, having a low risk of developing disease, and not presenting with two or more symptoms of a disease) men, women, and/or children.

In some embodiments, the reference level of an additional biomarker is a level of an additional biomarker present in a healthy subject (e.g., a subject that does not have a disease (e.g., any of the cardiac diseases described herein), has not been diagnosed as having a disease or condition associated with the biomarker, and/or is not presenting with two or more (e.g., two, three, four, or five) symptoms of a disease state or condition associated with the biomarker). In some embodiments, a reference level of an additional biomarker is a level of the additional biomarker from the same subject at an earlier point in time. In some embodiments, the reference level of an additional biomarker is a level of the additional biomarker from a subject that does not have a cardiac disease, has not been diagnosed as having a cardiac disease, and/or does not have two or more symptoms associated with a cardiac disease (e.g., arrhythmia, heart failure, heart attack, coronary artery disease, cardiovascular disease, acute coronary syndrome, and angina), inflammation, stroke, renal failure, obesity, high cholesterol, or dyslipidemia. In some embodiments, the reference level of an additional biomarker is a level of the additional biomarker from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina).

In some embodiments, the ratio of two different levels of an additional biomarker in a subject is determined and compared to a reference ratio of the additional biomarker. In some embodiments, the reference ratio of an additional biomarker can be a threshold ratio (e.g., a reference ratio of 1.00, 1.00, 1.1, 1.2, 1.3, 1.4, 1.5, 1.6, 1.7, 1.8, or 2.0). In some embodiments, the reference ratio of an additional biomarker is a ratio of two levels of the additional biomarker measured in a control subject (e.g., any of the control subjects described herein or the same subject). For example, a reference ratio of an additional biomarker can be a ratio of the levels of an additional biomarker collected at two different time points in a healthy subject (e.g., a subject that does not have a disease (e.g., any of the cardiac diseases described herein), has not been diagnosed as having a disease, and/or is not presenting with two or more (e.g., two, three, four, or five) symptoms of a disease state). In some embodiments, a reference ratio is a ratio of levels of an additional biomarker from the same subject at an earlier point in time. In some embodiments, the reference ratio of an additional biomarker is a ratio of the levels of an additional biomarker from a subject that does not have a cardiac disease, has not been diagnosed as having a cardiac disease, and/or does not have two or more symptoms associated with a cardiac disease (e.g., arrhythmia, heart failure, heart attack, coronary artery disease, cardiovascular disease, acute coronary syndrome, and angina). In some embodiments, the reference ratio is a ratio of levels of an additional biomarker from a subject that has not been diagnosed as having a cardiac disease and is not at risk for developing a cardiac disease (e.g., arrhythmia, heart failure, heart attack, coronary artery disease, cardiovascular disease, acute coronary syndrome, and angina).

Methods for determining the levels of these additional markers are known in the art. Kits for determining these additional markers are commercially available.

Methods for Selecting a Treatment for or Treating a Subject

Provided herein are methods of selecting a treatment for or treating a subject that include determining a level or ratio of soluble ST2 in a biological sample from a subject, comparing the level or ratio of soluble ST2 in the biological sample to a reference level or ratio of soluble ST2 (e.g., any of the reference levels of soluble ST2 described herein), and selecting, implanting, replacing, and/or reprogramming an implanted cardiac device, e.g., an ICD or CRT device, or a combination CRT and ICD (i.e. CRT-D) device, e.g., a cardiac device manufactured by Boston Scientific, Natick, Mass.), for a subject having an elevated level of soluble ST2 in the biological sample compared to the reference level of soluble ST2. Also provided are methods of selecting a treatment for or treating a subject that include determining a level of soluble ST2 in a first biological sample from a subject at a first time point, determining a level of soluble ST2 in a second biological sample obtained from the subject at a second time point, comparing the level of soluble ST2 in the first biological sample to the level of soluble ST2 in the second biological sample, and selecting, implanting, replacing, and/or reprogramming an implanted a cardiac device, e.g., an ICD device, CRT device, or CRT-D device, for a subject having an elevated level of soluble ST2 in the second biological sample compared to the level of soluble ST2 in the second biological sample. In some embodiments, the first and second time points are within two years (e.g., within 18 months, within 12 months, within 10 months, within 8 months, within 6 months, within 4 months, within 2 months, within 1 month, or within 1 week of each other).

In some embodiments, as an alternative or in addition to selecting a device, e.g., an ICD or CRT device, or a combination CRT and ICD (i.e. CRT-D) device, the method includes selecting and/or implementing a treatment that includes altering programming of a device already implanted in a subject based on ST2 levels or changes in ST2 concentrations. The programming of the device can be changed to alter the sensitivity and/or specificity of the detection algorithm. When ST2 levels are low and not changing over time, or dropping over time, there is a low probability of a true VTA occurring, and detection should be more specific and less sensitive, e.g., by a few percentage points. In contrast, in a subject with high levels of ST2 compared to the reference or when ST2 levels are increased, there is a high probability of true VTA occurring then you increase the sensitivity and lower the specificity. The programming parameters that embody this are:

1. Rate—Lower VTA detection rates are more sensitive, higher rates more specific.
2. Rhythm ID—Could be made variable.
3. Duration—Longer detection durations when true VTA is unlikely.
4. Therapy—Anti tachycardia Pacing (ATP) preferentially used before shocks when true VTA is unlikely.

In subjects who have received inappropriate shocks (i.e., when the device is too sensitive and is delivering a therapeutic shock when no arrhythmia is present), ST2 levels can be used to determine whether the programming should be altered. For example, in a subject who presently has a device, if the levels of ST2 in the subject are below a reference level and/or stable or dropping, then the device can be reprogrammed with lower sensitivity. If the levels of ST2 in the subject are elevated above a reference level and/or are increasing (i.e., the subject has a high or increasing risk of VTA) then the device should not be reprogrammed with lower sensitivity; the subject may just need to accept some inappropriate shocks. In some embodiments, the device is reprogrammed accordingly.

ST2 levels can also be used to determine whether a subject should have an implanted device replaced, e.g., at the end of the battery life. For example, in a subject who presently has a device, but has never had a therapy (e.g., never needed a shock from the device), ST2 levels can be used to determine whether the device should be replaced; if the levels of ST2 in the subject are below a reference level and/or stable or dropping, then the device need not be replaced. If the levels of ST2 in the subject are elevated above a reference level and/or are increasing (i.e., the subject has a high or increasing risk of VTA) then the device should be replaced. These methods can further include replacing the device.

In addition, the methods described above can include selecting a subject for a therapy, e.g., prioritizing subjects for treatment when factors such as time, cost, resources or device availability make it necessary to prioritize subjects. Based on levels of ST2 or changes in ST2 levels, subjects can be prioritized according to risk of a VTA; higher levels of ST2, and/or increasing levels of ST2 over time, are correlated with increased risk of VTA; these subjects should be prioritized over those with levels of ST2 that are lower and/or are stable or dropping.

Furthermore, the methods can include selecting a specific device for a subject, e.g., levels could be used to determine whether a subject should get a device that is a CRT (i.e. CRT-P) alone (e.g., a subject who has lower ST2 levels and thus a lower risk of VTA—though still an elevated risk) or CRT plus and ICD (i.e. CRT-D) (e.g., a subject who has higher ST2 levels and thus a higher risk of VTA). The methods can include comparing the ST2 levels in the subject to a reference as described above, e.g., a reference level or range of levels determines using methods known in the art, and the device selected based on the presence of a level of ST2 in the subject that falls above a certain threshold, or within a range of levels, or above the range. Some embodiments further include implanting the selected device (e.g., a CRT or a CRT plus an ICD) into the subject.

In some embodiments, the subject has been diagnosed as having a cardiac disease (e.g., arrhythmia, heart failure, heart attack, coronary artery disease, cardiovascular disease, acute coronary syndrome, and angina). In some embodiments, the subject has been identified as having an increased risk of developing a cardiac disease (e.g., arrhythmia, heart failure, heart attack, coronary artery disease, cardiovascular disease, acute coronary syndrome, and angina). In some embodiments, the subject has heart failure (e.g., chronic heart failure). In some embodiments, the subject has had at least one VTA event. In some embodiments, the subject may be female or male, and may be an adult or juvenile (e.g., an infant). Where the subject is an adult, the subject may be, e.g., between 18 to 20 years old or at least or about 20, 25, 30, 35, 40, 45, 50, 55, 60, 65, 70, 75, 80, 85, 90, 95, or at least or about 100 years old.

Some embodiments further include selection of a specific type of cardiac device, e.g., a ICD device, CRT device, or CRT-D device, for a subject determined to have an elevated level of soluble ST2 compared to the reference value of soluble ST2. Some embodiments further include recording the need for implantation of a cardiac device in a subject's clinical record or a clinical database. Some embodiments of the methods described herein include implanting the selected device into the subject. Some embodiments further include performing increased cardiac monitoring in a subject determined to have an elevated level of soluble ST2 compared to a reference level of soluble ST2 (e.g., increased periodicity of electrocardiograph examinations). Some embodiments further include recording the need for increased cardiac monitoring in the subject's clinical record or a clinical database. Some embodiments further include performing increased cardiac monitoring in the subject (e.g., increased frequency of clinic visits, initiating continuous cardiac monitoring, performing echography, and/or performing angioplasty). Some embodiments further include obtaining one or more biological samples from the subject.

The methods described herein can be performed by a medical professional (e.g., a physician, a physician's assistant, a nurse, a nurse's assistant, or a laboratory technician) or veterinary professional. These methods can be performed in a hospital, a clinic, a primary care facility (e.g., a nursing home or assisted living facility), or a clinical laboratory, or any combination thereof.

In some embodiments, the biological sample, the first biological sample, and/or the second biological sample are or contain blood, serum, or plasma. In some embodiments, the biological sample, the first biological sample, and/or the second biological sample are stored (e.g., at a temperature below 25° C., e.g., at a temperature below 15° C. or 0° C.) for a period of time (e.g., at least 2, 4, 6, 8, 10, 12, 24, 36, or 48 hours) prior to determining the level of soluble ST2 and/or determining the level of one or more additional biomarkers (e.g., BNP).

In some embodiments, the level of soluble ST2 is determined using an enzyme-linked immunosorbent assay (ELISA) (e.g., using any of the soluble ST2 ELISA kits described herein or known in the art, e.g., the PRESAGE kit). In some embodiments, the level of soluble ST2 is determined using an antibody described in WO 2011/127412, which is incorporated by reference herein.

In some embodiments, two or more levels of soluble ST2 are measured in biological samples (e.g., a first and second biological sample) from the subject. In these examples, an implanted cardiac device, e.g., an ICD, CRT, or CRT-D device, is selected for and/or implanted in a subject having an elevated level of soluble ST2 in a sample collected at a later time point (e.g., a second time point) compared to a level of soluble ST2 in a sample collected at an earlier time point (e.g., a first time point). In some embodiments where two levels of soluble ST2 are determined in a subject, a ratio of the levels of soluble ST2 in the subject is determined (the ratio of the level of soluble ST2 at the second time point compared to the level of soluble ST2 at the first time), the calculated soluble ST2 ratio is then compared to a reference ratio of soluble ST2 (e.g., any of the reference ratios of soluble ST2 described herein), and the methods further include selecting, implanting, replacing, or reprogramming an implanted cardiac device in or for a subject who has an elevated ratio of ST2 as compared to a reference ratio (indicating an increase in ST2 over time).

Some embodiments further include detecting a level of one or more additional biomarkers (e.g., any of the additional biomarkers described herein, e.g., BNP, proBNP, and NT-proBNP) in the biological sample, the first biological sample, and/or the second biological sample from the subject. In these embodiments, an implanted cardiac device, e.g., an ICD, CRT, or CRT-D device, is selected for and/or implanted in a subject having an elevation in the level of the one or more additional biomarkers in the biological sample, the first biological sample, and/or the second biological sample compared to a reference level of the one or more additional biomarkers. In some embodiments, the level of one or more additional biomarkers is determined in both the first biological sample and the second biological sample, a ratio of the level of the one or more additional biomarkers present in the second biological sample compared to the level of the one or more additional biomarkers present in the first biological sample is calculated, the calculated ratio of the one or more additional biomarkers is compared to a reference ratio of the one or more additional biomarkers (e.g., any of the reference ratios of an additional biomarkers described herein), and an implanted cardiac device, e.g., an ICD, CRT, or CRT-D device, is selected for a subject having an elevation in the calculated ratio of the one or more additional biomarkers compared to the reference ratio of the one or more additional biomarkers.

Some embodiments further include administering to the subject one or more (e.g., two, three, or four) pharmaceutical agents selected from the group of: nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin).

Methods for Determining the Risk of a VTA Event

Also provided are methods of evaluating the risk of a VTA event in a subject that include determining a level of soluble ST2 in a biological sample from a subject, comparing the level of soluble ST2 in the biological sample to a reference level of soluble ST2, and identifying a subject having an elevated level of soluble ST2 in the biological sample compared to the reference level of soluble ST2 as having an increased risk of a VTA event, or identifying a subject having no significant change or a decreased level of soluble ST2 in the biological sample compared to the reference level of soluble ST2 as having a decreased risk of a VTA event. In some embodiments, a subject having an elevated level of soluble ST2 (relative to a reference level of soluble ST2) has an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200%) of a VTA event. In some embodiments, a subject having no significant change or a decrease in the level of soluble ST2 compared to the reference level of soluble ST2 indicates has a decreased risk (e.g., a decreased risk of at least 10%, 15%, 20%, 25%, 30%, 35%, 40%, 45%, 50%, 55%, 60%, 65%, 70%, 75%, or 80%) of a VTA event.

Also provided are methods of evaluating the risk of a VTA event in a subject that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and identifying a subject having an elevated level of soluble ST2 in the second biological sample compared to the level of soluble ST2 in the first biological sample as having an increased risk of a VTA event. In some embodiments, a subject having an elevated level of soluble ST2 at the second time point relative to the level of soluble ST2 at the first time point has an increased risk (e.g., an increased risk of at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or 200%) of a VTA event. In some embodiments, a subject having no significant change or a decrease in the level of soluble ST2 at the second time point compared to the level of soluble ST2 at the first time point has a decreased risk (e.g., a decreased risk of at least 10%, 15%, 20%, 25%, 30%, 35%, 40%, 45%, 50%, 55%, 60%, 65%, 70%, 75%, or 80%) of a VTA event. In some embodiments, the VTA event is ventricular tachycardia, ventricular fibrillation, or ventricular flutter.

The above methods may be used to determine the risk of VTA event within 2 years (e.g., risk of a VTA event within 1 year, within 9 months, within 6 months, or within 30 days of the time at which the biological sample, the first biological sample, or the second biological sample was obtained from the subject).

In some embodiments, the subject has been diagnosed as having a cardiac disease (e.g., arrhythmia, heart failure, heart attack, coronary artery disease, cardiovascular disease, acute coronary syndrome, and angina). In some embodiments, the subject has been identified as having an increased risk of developing a cardiac disease (e.g., arrhythmia, heart failure, heart attack, coronary artery disease, cardiovascular disease, acute coronary syndrome, and angina). In some embodiments, the subject has heart failure (e.g., chronic heart failure). In some embodiments, the subject has an ICD or an implanted pacemaker (e.g., a medical device that provides CRT). In some embodiments, the subject has had at least one VTA event. In some embodiments, the subject may be female or male, and may be an adult or juvenile (e.g., an infant). Where the subject is an adult, the subject may be, e.g., between 18 to 20 years old or at least or about 20, 25, 30, 35, 40, 45, 50, 55, 60, 65, 70, 75, 80, 85, 90, 95, or at least or about 100 years old.

Some embodiments further include implantation of an ICD or performing CRT on a subject identified as having an increased risk of a VTA event. Some embodiments further include updating or recording the subject's risk of a VTA event (e.g., a subject's increased risk of a VTA event) in a clinical record or database. Some embodiments further include performing increased cardiac monitoring on a subject identified as having an increased risk of a VTA event (e.g., increased periodicity of electrocardiography testing). Some embodiments further include recording the need for increased cardiac monitoring in a clinical record or database for a subject identified as having an increased risk of a VTA event. Some embodiments further include informing the subject to self-monitor for the occurrence VTA events. Some embodiments of the methods described herein include performing increased cardiac monitoring in a subject identified as having an increased risk of a VTA event (e.g., increased frequency of clinic visits, initiating continuous cardiac monitoring, performing echography, and/or performing angioplasty).

In some embodiments, two or more levels of soluble ST2 are measured in biological samples (e.g., a first and second biological sample) from the subject. In these examples, a subject having an elevated level of soluble ST2 in a sample collected at a later time point (e.g., a second time point) compared to a level of soluble ST2 collected at an earlier time point (e.g., a first time point) is identified as having an increased risk of a VTA event. In some embodiments where two levels of soluble ST2 are determined in a subject, a ratio of the levels of soluble ST2 in the subject is determined (the ratio of the level of soluble ST2 at the second time point compared to the level of soluble ST2 at the first time), the calculated soluble ST2 ratio is then compared to a reference ratio of soluble ST2 (e.g., any of the reference ratios of soluble ST2 described herein), and a subject having an elevation in the calculated soluble ST2 ratio compared to the reference ratio of soluble ST2 is identified as having an increased risk of a VTA event. In some embodiments, a subject having no significant difference or a decrease in the calculated soluble ST2 ratio compared to the reference ratio of soluble ST2 is identified as having a decreased risk of a VTA event. Some embodiments of the methods described herein include performing increased cardiac monitoring in a subject identified as having an increased risk of a VTA event (e.g., increased frequency of clinic visits, initiating continuous cardiac monitoring, performing echography, and/or performing angioplasty). Some embodiments include decreasing the frequency of cardiac monitoring (e.g., decreasing the frequency of clinic visits, discontinuation of continuous cardiac monitoring, removing a device, or decreasing the dosage and/or frequency of one or more cardiovascular medications) for a subject identified as having a decreased risk of a VTA event.

Some embodiments further include detecting a level of one or more additional biomarkers (e.g., any of the additional biomarkers described herein, e.g., BNP, proBNP, and NT-proBNP) in a biological sample from the subject (e.g., the biological sample, the first biological sample, and/or the second biological sample). In these embodiments, a subject having an elevation in the level of the one or more additional biomarkers in the biological sample, the first biological sample, and/or the second biological sample as compared to a reference level of the one or more additional biomarkers is identified as having an elevated risk of having a VTA event. In some embodiments, a subject having no significant change or a decreased level of the one or more additional biomarkers compared to a reference level of the one or more additional biomarkers is identified as having a low or decreased risk of having a VTA event. In some embodiments, the level of one or more additional biomarkers is determined in both the first biological sample and the second biological sample, a ratio of the level of the one or more additional biomarkers present in the second biological sample to the level of the one or more additional biomarkers present in the first biological sample is calculated, the calculated ratio of the one or more additional biomarkers is compared to a reference ratio of the one or more additional biomarkers (e.g., any of the reference ratios of one or more additional biomarkers described herein), and a subject having an elevation in the calculated ratio of the one or more additional biomarkers compared to the reference ratio of the one or more additional biomarkers is identified as having an increased risk of a VTA event. In some embodiments, a subject having no significant change or a decrease in the calculated ratio of the one or more additional biomarkers compared to the reference ratio of the one or more additional biomarkers is identified as having a low or decreased risk of a VTA event.

Methods for Selecting a Subject for Participation, or Stratifying Subjects, in a Clinical Study Also provided are methods of selecting a subject for participation in, or stratifying subjects in, a clinical study of a treatment for reducing the risk of a VTA event that include determining a level of soluble ST2 in a biological sample from a subject, comparing the level of soluble ST2 in the biological sample to a reference level of soluble ST2, and selecting for participation a subject having an elevated level of soluble ST2 in the biological sample compared to the reference level of soluble ST2 in a clinical trial of a treatment for reducing the risk of a VTA event, or stratifying subjects in a clinical trial based on ST2 levels (e.g., based on tertiles, quartiles, or median ST2 levels). In some embodiments, a subject can be excluded from participation in a clinical study of a treatment for reducing the risk of a VTA event if the subject has no significant change or a decrease in the level of soluble ST2 in the biological sample compared to the reference level of soluble ST2 (e.g., any of the reference levels of soluble ST2 described herein).

Also provided are methods of selecting a subject for participation in, or stratifying subjects in, a clinical study for a treatment for reducing the risk of a VTA event that include determining a level of soluble ST2 in a first biological sample obtained from a subject at a first time point, determining a level of soluble ST2 in a second biological sample obtained from the subject at a second time point, comparing the level of soluble ST2 in the first biological sample to the level of soluble ST2 in the second biological sample, and selecting a subject having an elevated level of soluble ST2 in the second biological sample compared to the level of soluble ST2 in the first biological sample for participation in a clinical trial of a treatment for reducing the risk of a VTA event, or stratifying subjects in a clinical trial based on changing ST2 levels (e.g., based on tertiles, quartiles, or medians of change in ST2 levels). In some embodiments, a subject can be excluded from participation in a clinical study of a treatment for reducing the risk of a VTA event if the subject has no significant change or a decrease in the level of soluble ST2 at the second time point compared to the level of soluble ST2 determined at the first time point. In some embodiments, the treatment for reducing the risk of a VTA event is a pharmacological treatment (e.g., administration of one or more pharmaceutical agents) or the implantation of an implanted cardiac device, e.g., an ICD, CRT, or CRT-D device, In some embodiments, the subject has been diagnosed as having a cardiac disease (e.g., arrhythmia, heart failure, heart attack, coronary artery disease, cardiovascular disease, acute coronary syndrome, and angina). In some embodiments, the subject has been identified as having an increased risk of developing a cardiac disease (e.g., arrhythmia, heart failure, heart attack, coronary artery disease, cardiovascular disease, acute coronary syndrome, and angina).

In some embodiments, the subject has heart failure (e.g., chronic heart failure). In some embodiments, the subject has had at least one VTA event. In some embodiments, the subject may be female or male, and may be an adult or juvenile (e.g., an infant). Where the subject is an adult, the subject may be, e.g., between 18 to 20 years old or at least or about 20, 25, 30, 35, 40, 45, 50, 55, 60, 65, 70, 75, 80, 85, 90, 95, or at least or about 100 years old.

The clinical studies may be performed by a health care professional (e.g., a physician, a physician's assistant, a nurse, a phlebotomist, or a laboratory technician) in a health care facility (e.g., a hospital, a clinic, or a research center). The biological samples may be obtained from subjects that present with one or more (e.g., at least two, three, four, or five) symptoms of a disease state (e.g., arrhythmia, cardiovascular disease, angina, or heart failure), subjects that are admitted in a hospital, or subjects who are asymptomatic.

In some embodiments, two or more levels of soluble ST2 are measured in biological samples (e.g., a first and second biological sample) from the subject. In these examples, a subject having an elevated level of soluble ST2 in a sample collected at a later time point (e.g., a second time point) compared to a level of soluble ST2 collected at an earlier time point (e.g., a first time point) is selected for participation in a clinical study of a treatment for reducing the risk of a VTA event, or stratified based on the change in ST2 levels. In some embodiments where two levels of soluble ST2 are determined in a subject, a ratio of the levels of soluble ST2 in the subject is determined (the ratio of the level of soluble ST2 at the second time point compared to the level of soluble ST2 at the first time), the calculated soluble ST2 ratio is then compared to a reference ratio of soluble ST2 (e.g., any of the reference ratios of soluble ST2 described herein), and a subject having an elevation in the calculated soluble ST2 ratio compared to the reference ratio of soluble ST2 is selected for participation in a clinical study of a treatment for reducing the risk of a VTA event. In some embodiments, a subject having no significant difference or a decrease in the calculated soluble ST2 ratio compared to the reference ratio of soluble ST2 is not selected or excluded from participation in a clinical study for a treatment for reducing the risk of a VTA event.

Some embodiments further include detecting a level of one or more additional biomarkers (e.g., any of the additional biomarkers described herein, e.g., BNP, proBNP, and NT-proBNP) in a biological sample from the subject (e.g., the biological sample, the first biological sample, and/or the second biological sample). In these embodiments, a subject having an elevation in the level of the one or more additional biomarkers in the biological sample, the first biological sample, and/or the second biological sample as compared to a reference level of the one or more additional biomarkers is selected for participation in a clinical study of a treatment for reducing the risk of a VTA event. In some embodiments, a subject having no significant change or a decreased level of the one or more additional biomarkers compared to a reference level of the one or more additional biomarkers is not selected or is excluded from participation in a clinical study of a treatment for reducing the risk of a VTA event. In some embodiments, the level of one or more additional biomarkers is determined in both the first biological sample and the second biological sample, a ratio of the level of the one or more additional biomarkers present in the second biological sample compared to the level of the one or more additional biomarkers present in the first biological sample is calculated, the calculated ratio of the one or more additional biomarkers is compared to a reference ratio of the one or more additional biomarkers (e.g., any of the reference ratios of an additional biomarkers described herein), and a subject having an elevation in the calculated ratio of the one or more additional biomarkers compared to the reference ratio of the one or more additional biomarkers is selected for participation in a clinical study of a treatment for reducing the risk of a VTA event. In some embodiments, a subject having no significant change or a decrease in the calculated ratio of the one or more additional biomarkers compared to the reference ratio of the one or more additional biomarkers is not selected or is excluded from participation in a clinical study of a treatment for reducing the risk of a VTA event.

Additional factors may further indicate that the subject should be included in a clinical study of a treatment for reducing the risk of a VTA event. Non-limiting examples of these additional factors include: prior diagnosis with cardiovascular disease, angina, heart attack, heart failure, renal failure, inflammation, or stroke; or presentation of one or more (e.g., two, three, or four) of the following symptoms: shortness of breath, heart palpitations, increased heart rate, weakness, dizziness, nausea, sweating, chest discomfort or pressure, chest pain, arm pain, chronic fullness, indigestion, sweating, wheezing, sleep apnea, and anxiety. Additional exemplary factors that indicate that a subject should be included in a clinical study of a treatment for reducing the risk of a VTA include a BMI of 25-30, a BMI of greater than 30, reduced LV EF% (e.g., an EF<35%); cardiac dis-synchrony (as measured by QRS width, e.g., QRS>120 ms) or continued therapy with one or more (e.g., at least two, three, four, or five) pharmaceutical agents selected from the group of nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin).

Kits

Also provided are kits for use in a method described herein containing one or more antibodies that specifically binds to soluble ST2, optionally reagents for detection and/or quantifying binding of the antibodies to soluble ST2 in a sample, and optionally instructions for using the kit (e.g., the antibodies in the kit) to perform one or more methods described herein. The antibody that specifically binds ST2 can be polyclonal, monoclonal, or recombinant, e.g., chimeric or humanized, fully human, non-human, e.g., murine, mono-specific, or a single-chain antibody. Any of the kits described herein may also be provided as an ELISA assay (e.g., may further include one or more secondary antibodies and/or a substrate for detection). For example, any of the kits described herein may include an antibody produced from the hybridoma deposited at American Type Culture Collection and designated by Patent Deposit Designation PTA-10432, or any of the exemplary anti-ST2 antibodies described in WO 2011/127412 or U.S. Patent Application Publication No. 2011/0256635.

Any of the kits described herein may also include one or more (e.g., two, three, four, or five) additional antibodies for one or more (e.g., two, three, four, or five) additional markers selected from the group of: proANP, NT-proANP, ANP, proBNP, NT-proBNP, BNP, troponin, CRP, galectin, creatinine, liver function enzymes, albumin, endothelin-1, endothelin-1, and bacterial endotoxin. Antibodies for ST2, galectin, proANP, NT-proANP, ANP, proBNP, NT-proBNP, BNP, troponin, CRP, creatinine, liver function enzymes, albumin, endothelin-1, and bacterial endotoxin are commercially available.

The invention is further described in the following example, which does not limit the scope of the invention described in the claims.

EXAMPLES

Example 1

Soluble ST2 can be Used to Assess the Risk of a VTA in Subjects with Stable Heart Failure A set of experiments was performed to determine if soluble ST2 (ST2) is useful for predicting the occurrence of VTA events in stable class I/II heart failure patients who were receiving treatment with an ICD or CRT-D (subjects enrolled in the MADIT-CRT trial). A schematic of the MADIT-CRT study design is shown in FIG. 1. The MADIT-CRT is the largest randomized NYHA Class I/II ICD/CRT-D trial to date. A total of 1820 patients were enrolled in this study at 110 centers in 14 countries. The average follow-up time for subjects participating in this study was 34.3 months. Commercially available devices were used in these studies (Boston Scientific, Natick, Mass.).

In these experiments, soluble ST2 and BNP levels were measured at baseline and at 1 year in patients participating in this MADIT-CRT (Multicenter Automatic Defibrillator Implantation Trial—Cardiac Resynchronization Therapy) sub-study (N=684 and 1197, respectively). An appropriate anti-arrhythmic therapy for VTA (including ventricular tachycardia, ventricular fibrillation, and ventricular flutter) was decided by a core lab. Survival models were used to assess the prognostic value of baseline ST2 and change in ST2 from baseline to 12 months of time to VTA. Levels of BNP were determined using a commercially available ELISA assay (BAYER). The levels of soluble ST2 were determined using a commercially available ELISA (Presage® ST2 Assay, Critical Care Diagnostics, San Diego, Calif.) according to the manufacturer's instructions.

The primary outcome to be assessed in these studies was the time to the first occurrence of appropriate anti-arrhythmic therapy for a VTA event. A VTA event includes ventricular tachycardia (VT), ventricular fibrillation (VF), and/or ventricular flutter (VFL). For the purposes of these experiments, a VT was defined as the ventricular rate up to 250 beats/minute, a VF was defined as a ventricular rate faster than 250 beast/minute with disorganized ventricular electrograms, a VFL was defined as a ventricular rate faster than 250 beats/minute and monomorphic, and an anti-arrhythmic therapy was defined as any type of therapy that was rendered including anti-tachycardia pacing and cardiac shock.

Figure 2:
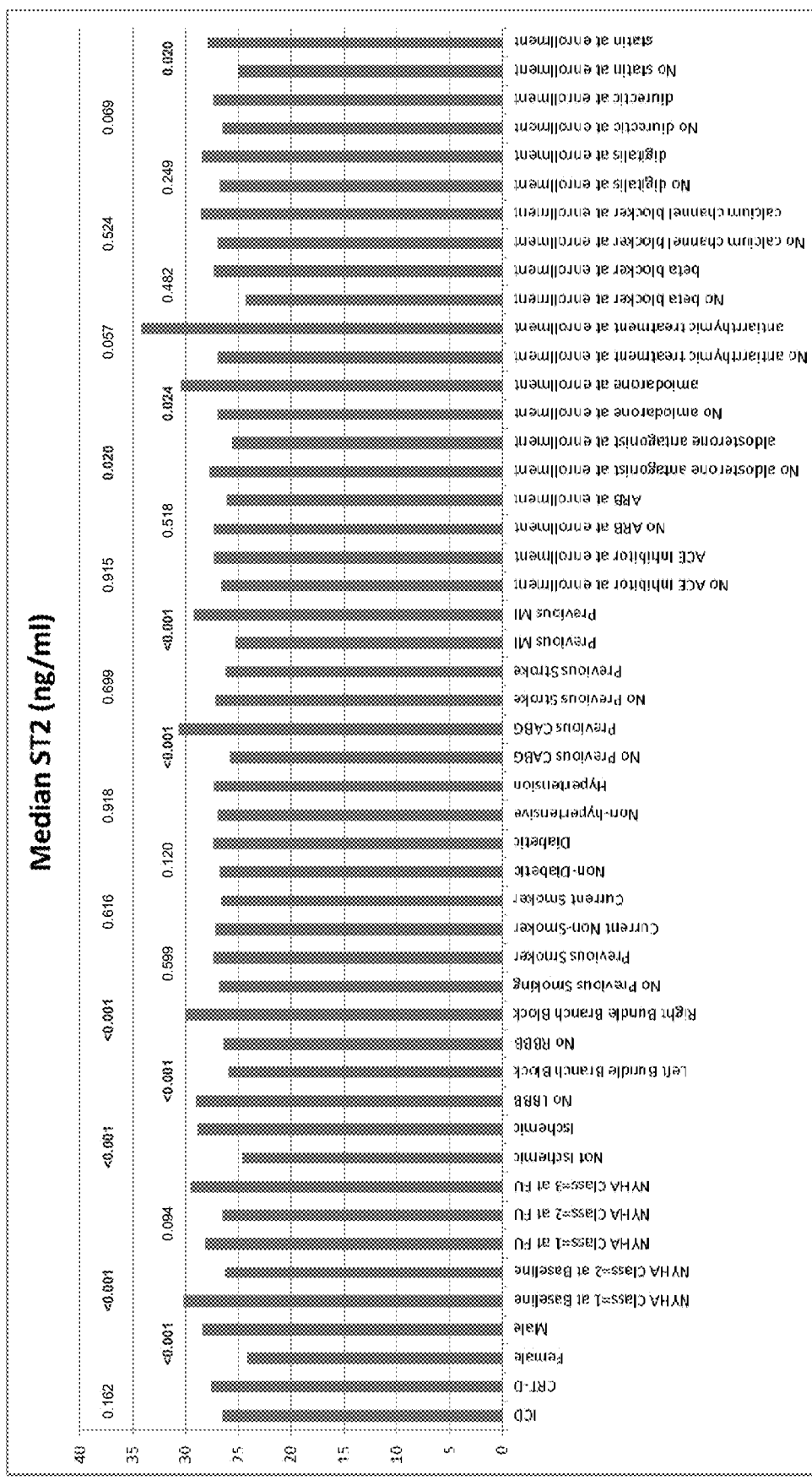
FIG. 2 is a graph showing the baseline soluble ST2 levels in different patient subgroups participating in the MADIT-CRT clinical study.

The data show that baseline ST2 levels were significantly higher in male, NYHA class I, right bundle branch block, ischemic, prior CABG, and prior MI subgroups (see, FIG. 2, all P<0.001). Higher baseline levels were also associated with amiodarone (p=0.024) and statin (p=0.020) use, and the lack of aldosterone use at baseline (p=0.020) (FIG. 2).

Trends for increased risk of VTA were found with log-transformed (ln) ST2 and lnBNP at baseline (HR 1.6 [95% CI 0.99-2.6], P=0.056 and HR 1.11 [95% CI 1-1.23], P=0.051 respectively). The baseline soluble ST2 levels were also prognostic of device therapy for VTA On(ST2): HR=1.6 (0.99-2.6); p=0.058).

A small increase in ST2 levels from baseline to 12 months (0.06 ng/mL (IQR: -3.9-6.0 ng/mL) was blunted by CRT treatment (ICD: median 1.04 fold increase; IQR=0.89-1.32; CRT-D: median fold increase 1.02; IQR=0.86-1.19; Kruskal-Wallis test p=0.0365).

Figure 3:
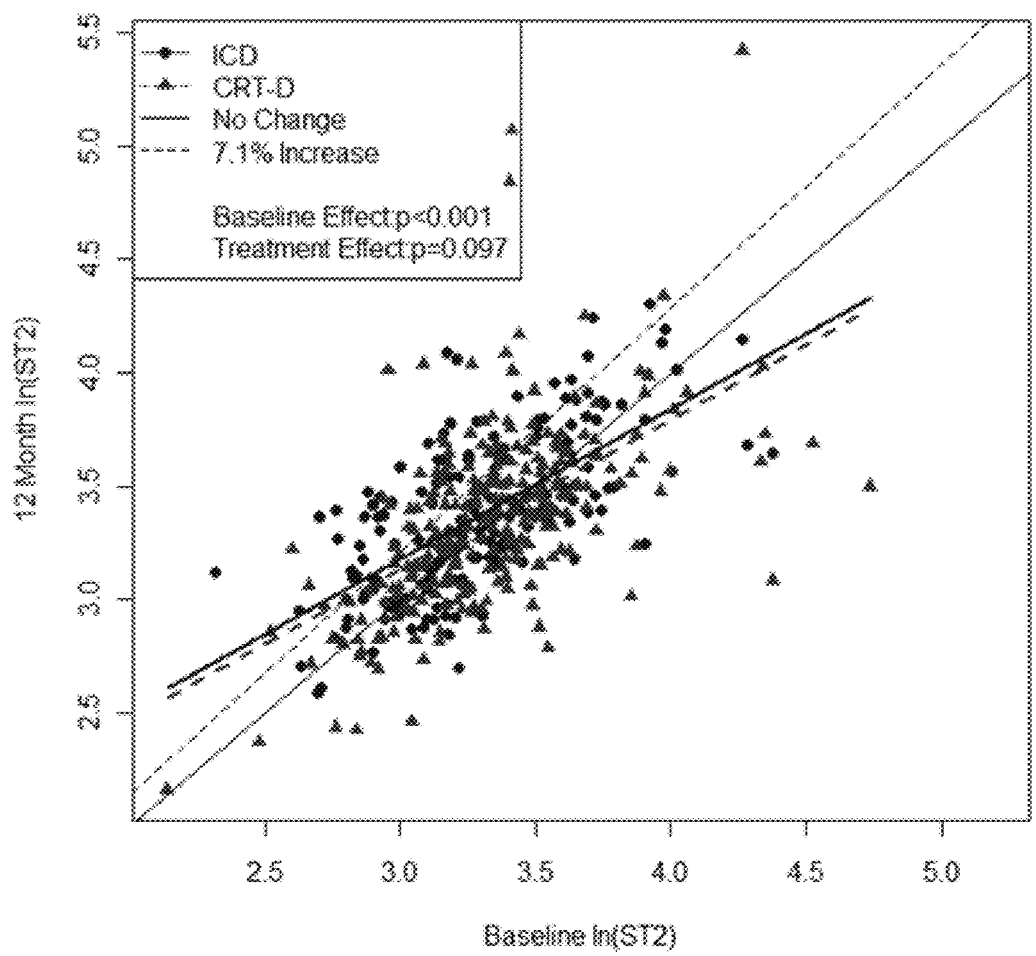
FIG. 3 is a graph of the natural logarithm of soluble ST2 levels determined at baseline and at 12-months in patients that have received an ICD (circles) or CRT (squares).
Figure 4:
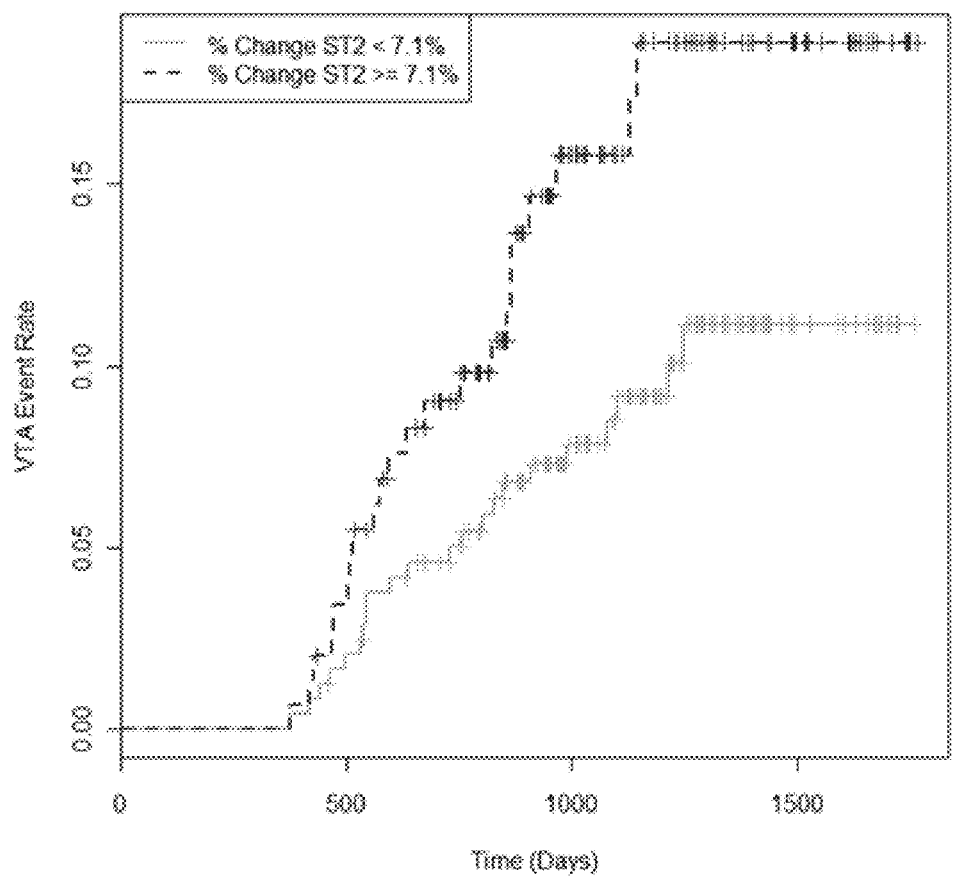
FIG. 4 shows two Kaplan-Meier survival curves showing the VTA event rate over time for subjects having less than a <7.1% change in soluble ST2 levels, and subjects having greater than or equal to 7.1% change in soluble ST2 levels.

Multivariate analysis demonstrated that the difference of ln ST2 levels from baseline to 12 months was independently predictive for VTA (HR 3.71 [95% CI 1.4-9.8]; p=0.008). The change in soluble ST2 levels was prognostic of VTA after 1 year (ln(ΔST2): HR=3.8 (1.45-9.99); p=0.008). In the 42% of the patients with an ST2 increase of more than 7.1%, the risk of VTA increased by 2.25-fold (95% CI 1.2-4.1; p=0.008) (FIGS. 3 and 4). The change in ST2 remained predictive even after controlling for changes in BNP, LVEF, LVESV, and LVEDV (P=0.0048).

Figure 5:
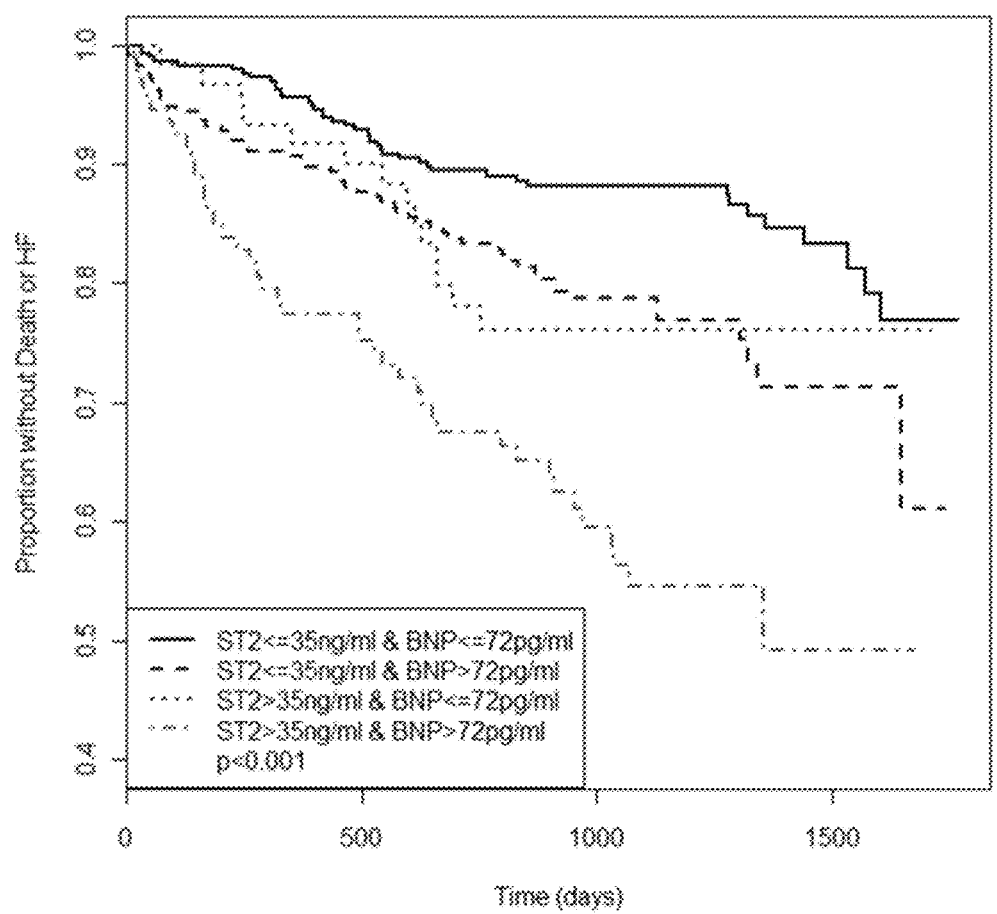
FIG. 5 shows Kaplan-Meier curves of all-cause mortality or heart failure for subjects having: levels of soluble ST2 less than or equal to 35 ng/mL and BNP less than or equal to 72 pg/mL; levels of soluble ST2 less than or equal to 35 ng/mL and a BNP of greater than 72 pg/mL; levels of soluble ST2 greater than 35 ng/mL and BNP of less than or equal to 72 pg/mL; and levels of soluble ST2 greater than 35 ng/mL and BNP of greater than 72 pg/mL.

The baseline soluble ST2 levels were also prognostic of all-cause mortality or heart failure events in these subjects (ln(ST2): HR=2.19 (1.45-3.33); p<0.001) (tertiles of ST2; p=0.01) (ST2 divided at its traditional cut point of 35 ng/mL: HR=2.2 (1.58-3.08); p<0.001). The prognostic value of all-cause mortality holds after controlling for baseline risk factors. Baseline soluble ST2 divided at its traditional cut point (35 pg/mL) and BNP divided at the median value (72 pg/mL) was also prognostic of all-cause mortality or heart failure events (FIG. 5; p<0.001).

In sum, the data show that serial measurement of ST2 may be a valuable tool for monitoring stable patients with mild HF for risk of future arrhythmias, and that levels of soluble ST2 can be used to identify subjects that would benefit from CRT or an ICD, identify a subjects at risk of having a VTA, and to select a therapy for a subject (e.g., determine whether a subject should receive CRT or be implanted with an ICD).

What is claimed is:

1. A method for selecting a treatment for a subject having heart failure to reduce the risk of a ventricular tachyarrhythmia (VTA) event, the method comprising:
   determining a first level of soluble ST2 in a biological sample comprising blood, serum or plasma obtained from a subject having heart failure at a first time point;
   determining a second level of soluble ST2 in a biological sample comprising blood, serum or plasma obtained from the subject at a second time point;
   identifying a subject having an elevated second level of soluble ST2 as compared to the first level of soluble ST2 as being more likely to benefit from implantation of an implantable cardiac defibrillator (ICD), a cardiac resynchronization therapy device (CRT), or a combination cardiac resynchronization therapy defibrillator device (CRT-D); and
   selecting an ICD, a CRT, or a CRT-D for the identified subject.

2. The method of claim 1, wherein the subject has previously had at least one ventricular tachyarrhythmia event.

3. The method of claim 1, wherein the method comprises selecting an ICD for the identified subject.

4. The method of claim 1, wherein the method comprises selecting a CRT for the identified subject.

5. The method of claim 1, wherein the method comprises selecting a CRT-D for the identified subject.

6. A method of treating a subject having heart failure to reduce the risk of a ventricular tachyarrhythmia (VTA) event, the method comprising:
   determining a first level of soluble ST2 in a biological sample comprising blood, serum, or plasma from a subject having heart failure;

determining a second level of soluble ST2 in a biological sample comprising blood, serum, or plasma from the subject;

identifying a subject having an elevated second level of soluble ST2 in the biological sample compared to the first level of soluble ST2 as being more likely to benefit from implantation of an implantable cardiac defibrillator (ICD), a cardiac resynchronization therapy device (CRT), or a combination cardiac resynchronization therapy defibrillator device (CRT-D); and implanting an ICD, a CRT, or a CRT-D device into the identified subject, or replacing or reprogramming an implanted ICD, CRT, or CRT-D in the identified subject.

7. The method of claim 6, wherein the subject has previously had at least one ventricular tachyarrhythmia event.

8. The method of claim 6, wherein the method comprises implanting an ICD into the identified subject.

9. The method of claim 6, wherein the method comprises implanting a CRT into the identified subject.

10. The method of claim 6, wherein the method comprises implanting a CRT-D into the identified subject.

11. The method of claim 6, wherein the method comprises replacing an implanted ICD in the identified subject.

12. The method of claim 6, wherein the method comprises replacing an implanted CRT in the identified subject.

13. The method of claim 6, wherein the method comprises replacing an implanted CRT-D in the identified subject.

14. The method of claim 6, wherein the method comprises reprogramming an implanted ICD in the identified subject.

15. The method of claim 6, wherein the method comprises reprogramming an implanted CRT in the identified subject.

16. The method of claim 6, wherein the method comprises reprogramming an implanted CRT-D in the identified subject.

* * * * *